(12) United States Patent
Rafii et al.

(10) Patent No.: US 8,043,803 B2
(45) Date of Patent: Oct. 25, 2011

(54) SLITRKS AS MARKERS FOR STEM AND PROGENITOR CELLS AND METHODS OF USE THEREOF

(75) Inventors: Shahin Rafii, New York, NY (US); Till Milde, Roosevelt Island, NY (US); Sergey V. Shmelkov, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 779 days.

(21) Appl. No.: 11/951,761

(22) Filed: Dec. 6, 2007

(65) Prior Publication Data

US 2008/0267922 A1 Oct. 30, 2008

Related U.S. Application Data

(60) Provisional application No. 60/873,196, filed on Dec. 6, 2006.

(51) Int. Cl.
*C12Q 1/68* (2006.01)

(52) U.S. Cl. .......................................... 435/6; 435/325

(58) Field of Classification Search .................. None
See application file for complete search history.

(56) References Cited

U.S. PATENT DOCUMENTS 5,514,539 A * 5/1996 Bukh et al. ................... 435/5
6,670,123 B1 12/2003 Belyavsky et al.

OTHER PUBLICATIONS

Hackney JA et al. 2002. A molecular profile of a hematopoietic stem cell niche. Proc Natl Acad Sci USA 99: 13061-13066.*
Terskikh AV et al. 2001. From hematopoiesis to neuropoiesis: Evidence of overlapping genetic programs. Proc Natl Acad Sci USA 98: 7934-7939.*
Abelson et al., "Sequence variants in slitrkl are associated with Tourette's syndrome," Science;3 10(5746):3 17-320 (Oct. 14, 2005).
Aruga et al., "Human slitrk family genes: genomic organization and expression profiling in normal brain and brain tumor tissue," Gene;3 1537-94 (Oct. 2, 2003).
Aruga et al., "Identification and characterization of Slitrk, a novel neuronal transmembrane protein family controlling neurite outgrowth," Mol Cell Neurosci;24(1): 117-129 (Sep. 2003).
Asahara et al., "Isolation of putative progenitor endothelial cells for angiogenesis." Science;275(5302):964-967 (Feb. 14, 1997).
Baum et al.,."Isolation of a candidate human hematopoietic stem-cell population," Proc Natl Acad Sci U S A;8(7):2804-2808 (Apr. 1, 1992).
Bonnet et al., "Human acute myeloid leukemia is organized as a hierarchy that originates from a primitive hematopoietic cell," Nat Med.;3(7):730-737 (Jul. 1997).
Civin et al., "Antigenic analysis of hematopoiesis. 111. A hematopoietic progenitor cell surface antigen defined by a monoclonal antibody raised against KG-la cells," J Immunol.; 133(1): 157-165 (Jul. 1984).
Folkman J., Angiogenesis-dependent diseases. Semin Oncol. ;28(6):536-542 (Dec. 2001).
Goodell et al., "Isolation and functional properties of murine hematopoietic stem cells that are replicating in vivo,"J Exp Med. ;183(4): 1797-1806 (Apr. 1, 1996).
Nador et al., "Primary effusion lymphoma: a distinct clinicopathologic entity associated with the Kaposi's sarcoma-associated herpes virus,";88(2):645-656 (Jul. 15, 1996).
Okada et al., "Enrichment and characterization of murine hematopoietic stem cells that express c-kit molecule," Blood.;78(7): 1706-1712 (Oct. 1, 1991).
Osawa et al., Long-term lymphohematopoietic reconstitution by a single CD34-lowlnegative hematopoietic stem cell, Science;273(5272):242-245 (Jul. 12, 1996).
Park et al., "Establishment and maintenance of human embryonic stem cells on STO, a permanently growing cell line," Biol Reprod. ;69(6):2007-2014 (Dec. 2003).
Rafii et al., "Therapeutic stem and progenitor cell transplantation for organ vascularization and regeneration," Nat Med.;9(6):702-712 (Jun. 2003).
Shmelkov et al., "Two-dimensional gene expression fingerprinting," Anal Biochem;290(1):26-35 (Mar 1, 2001).
Simonelli et al., Clinical features and outcome of primary effusion lymphoma in HIV-infected patients: a single-institution study. J Clin Oncol.;21(21):3948-3954 (Nov. 1, 2003).
Vincent et al., Fetal stromal-dependent paracrine and intracrine vascular endothelial growth factor-alvascular endothelial growth factor receptor-1 signaling promotes proliferation and motility of human primary myeloma cells. Cancer Res.;65(8):3 185-3 192 (Apr. 15, 2005).
Yin et al., "AC133, a novel marker for human hematopoietic stem and progenitor cells," Blood;90(12):5002-5012 (Dec. 15, 1997).

* cited by examiner

*Primary Examiner* — Lora E Barnhart
(74) *Attorney, Agent, or Firm* — Wilmer Cutler Pickering Hale and Dorr LLP

(57) ABSTRACT

The present invention relates to slitrk proteins as markers of stem and progenitor cells, including embryonic stem cells and hematopoietic stem and progenitor cells, and also as a marker of leukemia and lymphoma cells, and of endothelial cells. The invention provides, inter alia, methods for purifying slitrk-positive cells, methods for detecting slitrk-positive cells, purified preparations of slitrk-positive cells, therapeutic compositions containing purified slitrk-positive cells, methods for targeting therapeutic agents to slitrk-positive cells, and methods of treatment, including but not limited to, methods of administering slitrk-positive cells to subjects in need thereof.

12 Claims, 7 Drawing Sheets

Figure 4
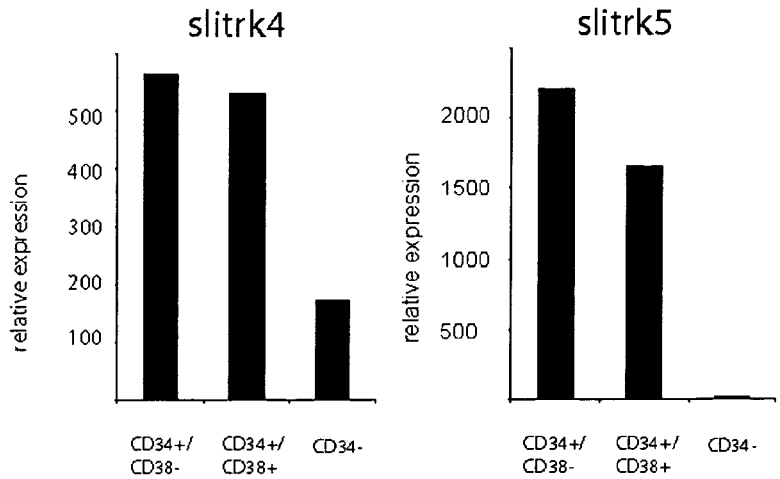
A  bone marrow
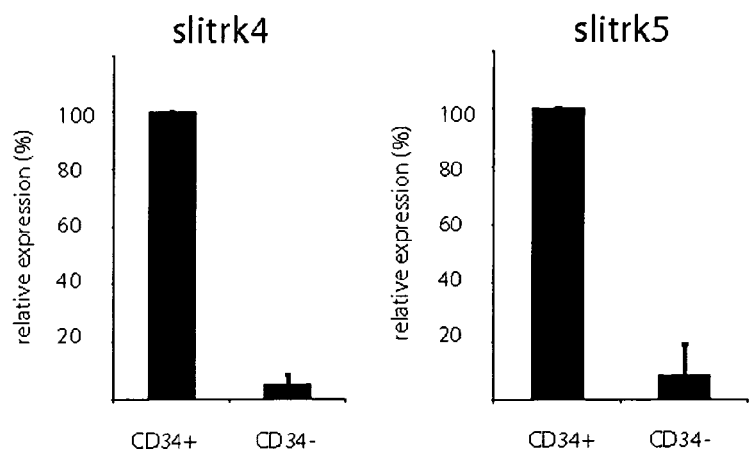
B  cord blood
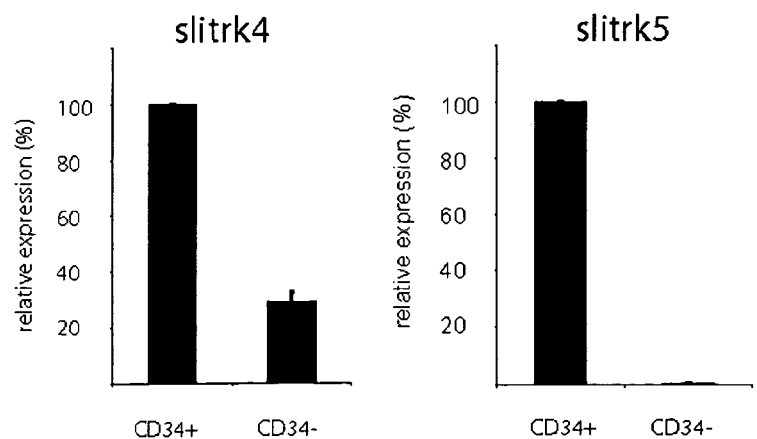
C  mobilized peripheral blood

SLITRKS AS MARKERS FOR STEM AND PROGENITOR CELLS AND METHODS OF USE THEREOF

This application claims benefit under 35 U.S.C. §119 of U.S. provisional application No. 60/873,196, filed on Dec. 6, 2006, the disclosure of which is hereby incorporated by reference.

This invention was supported, in part, by NIH grant R01-HL075234 to Dr. Shahin Rafii. Therefore, the U.S. government may have certain rights to this invention. All publications, patent applications, patents, and other references mentioned herein are incorporated by reference in their entirety.

FIELD OF THE INVENTION

The present invention relates to slitrks as markers for stem and progenitor cells, including embryonic stem cells and hematopoietic stem and progenitor cells, and also to slitrks as markers for cancer cells such as leukemia and lymphoma cells, and endothelial cells, and to methods of use of such cell markers, for example in isolating or detecting slitrk-expressing cells. The invention also relates, inter alia, to methods of methods for targeting therapeutic agents to cells expressing slitrks and to methods of identifying drugs that act on slitrks or on slitrk-expressing cells. In certain embodiments, the present invention relates to slitrk-expressing leukemia and lymphoma cells, and to methods of detection of such cells, and methods of treatment of leukemias and lymphomas.

BACKGROUND OF THE INVENTION

Stem cell research has the potential to change the face of medical and veterinary science by providing cells that can be used therapeutically to repair specific tissues and organs in the body. The ability to detect, purify, and grow such therapeutically useful stem cells, from both embryonic and adult tissues, has been hampered by a lack of specific markers. The present invention addresses these and other needs in the art by providing markers for stem and progenitor cells, and methods of use thereof.

In addition, there is a need for markers of cancer cells. Methods of detecting cancer cells, and also methods of targeting therapeutic agents to such cancer cells and methods of treatment of cancers, are needed. The present invention addresses these and other needs in the art by providing markers for cancer cells, such as leukemia and lymphoma cells, and methods of use thereof.

SUMMARY OF THE INVENTION

The present invention relates to the discovery that the family of transmembrane proteins referred to as "slitrks" are markers for undifferentiated multipotent stem and progenitor cells, such as embryonic stem cells and fetal stem and progenitor cells, and also for adult stem cells, such as hematopoietic stem and progenitor cells, and are also markers for certain cancer cells, such as leukemia and lymphoma cells, and also endothelial cells. The present invention provides, inter alia, methods for enriching or isolating such slitrk-positive cells, methods for detecting slitrk-positive cells, purified preparations of slitrk-positive cells, and therapeutic compositions containing such cells. The present invention also provides methods of treatment of subjects, such as human subjects, by administration of slitrk-positive stem or progenitor cells, or by administration of differentiated cells derived from slitrk-positive stem or progenitor cells. For example, the present invention provides methods for reconstituting or supplementing stem or progenitor cell populations in subjects in need thereof, and methods of treating disorders of the hematopoietic system. Such treatment methods include autologous stem and progenitor cell transplantation methods, such as autologous hematopoietic stem cell transplantation methods. Such methods may be particularly useful for patients undergoing chemotherapy or radiation therapy. The present invention also provides methods that may be useful for the detection, diagnosis and treatment of cancers, in particular leukemias and lymphomas. These and other aspects of the invention are described herein.

In a first embodiment, the present invention provides a method for enriching, isolating, separating or purifying slitrk-positive stem or progenitor cells from a mixed population of cells, comprising obtaining a mixed population of cells, contacting the mixed population of cells with an agent that binds to a slitrk protein selected from the group consisting of slitrk1, slitrk2, slitrk3, slitrk4, slitrk5 and slitrk6, and separating the cells bound by the agent from cells that are not bound by the agent, wherein the cells bound by the agent comprise slitrk-positive stem or progenitor cells.

In a second embodiment, the present invention provides a method for detecting slitrk-positive stem or progenitor cells in a tissue, a tissue sample or a cell population, comprising obtaining a tissue, a tissue sample or a cell population, contacting the tissue, the tissue sample or the cell population with an agent that binds to a slitrk protein selected from the group consisting of slitrk1, slitrk2, slitrk3, slitrk4, slitrk5 and slitrk6, and determining whether the agent has bound to the tissue, the tissue sample or the cell population, wherein binding indicates the presence of slitrk-positive stem or progenitor cells.

In a third embodiment, the present invention provides a method for detecting slitrk-positive stem or progenitor cells in a tissue, a tissue sample or a cell population, comprising obtaining a tissue, a tissue sample or a cell population, and determining whether the tissue, the tissue sample or the cells contains a slitrk mRNA selected from the group consisting of slitrk1, slitrk2, slitrk3, slitrk4, slitrk5 and slitrk6, wherein the presence of slitrk mRNA indicates the presence of slitrk-positive stem or progenitor cells.

In a fourth embodiment, the present invention provides a substantially pure preparation of slitrk-expressing stem or progenitor cells. The stem or progenitor cells may be selected from the group consisting of embryonic stem cells, fetal stem cells, hematopoietic stem cells, and mononuclear cells. The present invention also provides therapeutic compositions containing such substantially pure preparations of slitrk-expressing stem or progenitor cells and a therapeutically acceptable carrier.

In a fifth embodiment, the present invention provides methods of treatment comprising administering to a subject in need thereof a substantially pure preparation of slitrk-expressing stem or progenitor cells, such as hematopoietic stem or progenitor cells.

In a sixth embodiment, the present invention provides a method of treatment comprising administering to a subject in need thereof a composition comprising differentiated cells derived in vitro from slitrk-positive stem or progenitor cells.

In a seventh embodiment, the present invention provides autologous transplantation methods for delivering stem or progenitor cells to a subject in need thereof, comprising obtaining a tissue sample from a subject, purifying slitrk-positive stem or progenitor cells and administering the purified slitrk-positive stem or progenitor cells to the subject.

In an eighth embodiment, the present invention provides methods for detecting leukemia or lymphoma cells in a tissue, a tissue sample or a cell population, comprising obtaining a tissue, a tissue sample or a cell population, contacting the tissue, the tissue sample or the cell population with an agent that binds to a slitrk protein selected from the group consisting of slitrk1, slitrk2, slitrk3, slitrk4, slitrk5, and slitrk6, and determining whether the agent has bound to the tissue, the tissue sample or the cell population, wherein binding indicates the presence of leukemia or lymphoma cells.

In a ninth embodiment, the present invention provides methods for detecting leukemia or lymphoma cells in a tissue, a tissue sample or a cell population, comprising obtaining a tissue, a tissue sample or a cell population, and determining whether the tissue, the tissue sample or the cells contains a slitrk mRNA selected from the group consisting of slitrk1, slitrk2, slitrk3, slitrk4, slitrk5, and slitrk6 mRNA, and wherein the presence of slitrk mRNA indicates the presence of leukemia or lymphoma cells.

In a tenth embodiment, the present invention provides methods of targeting therapeutic agents to leukemia or lymphoma cells in a subject, comprising conjugating a therapeutic agent to an agent that binds to a slitrk protein to generate a conjugated agent, and administering the conjugated agent to the subject.

In an eleventh embodiment, the present invention provides a method of treating leukemia or lymphoma in a subject comprising administering to the subject an agent that inhibits the function of a slitrk protein, such as, for example, a function-blocking humanized monoclonal antibody.

In a twelfth embodiment, the present invention provides a method for identifying agents having anti-leukemia or anti-lymphoma activity. For example, the present invention provides a method for identifying agents having anti-leukemia or anti-lymphoma activity, comprising providing one or more slitrk proteins, contacting the one or more slitrk proteins with a library of agents, identifying at least one agent from the library that binds to at least one of the slitrk proteins, and testing the slitrk-binding agents to identify agents that kill, or inhibit the proliferation of, leukemia or lymphoma cells.

The present invention also relates to slitrks as markers for endothelial cells, and provides, inter alia, methods for enriching, isolating, separating or purifying slitrk-positive endothelial cells, methods for detecting slitrk-positive endothelial cells, substantially pure preparations of slitrk-expressing endothelial cells, methods of treatment comprising administering to a subject in need thereof a substantially pure preparation of slitrk-expressing endothelial cells, and methods of targeting therapeutic agents to slitrk-positive endothelial cells. In preferred embodiments, the present invention relates to slitrk4 and slitrk5-positive endothelial cells.

These and other embodiments of the invention are described further in the accompanying written description, drawings, and claims.

BRIEF DESCRIPTION OF THE DRAWINGS

FIG. 4 shows expression of slitrk4 and slitrk5 by human hematopoietic stem and progenitor cells. Panel A shows the relative expression of slitrk4 and slitrk5 in hematopoietic stem cells isolated from adult bone marrow (qPCR). Panels B and C show the relative difference of slitrk4 and slitrk5 expression in CD34+ and CD34− populations isolated from cord blood and mobilized peripheral blood (qPCR). Expression of slitrk4 or slitrk5 in CD34− cells is represented as the percentage of the CD34+ population. Error bars represent standard error of mean (n=3 independent experiments).

DETAILED DESCRIPTION OF THE INVENTION

Abbreviations

Figure 1:
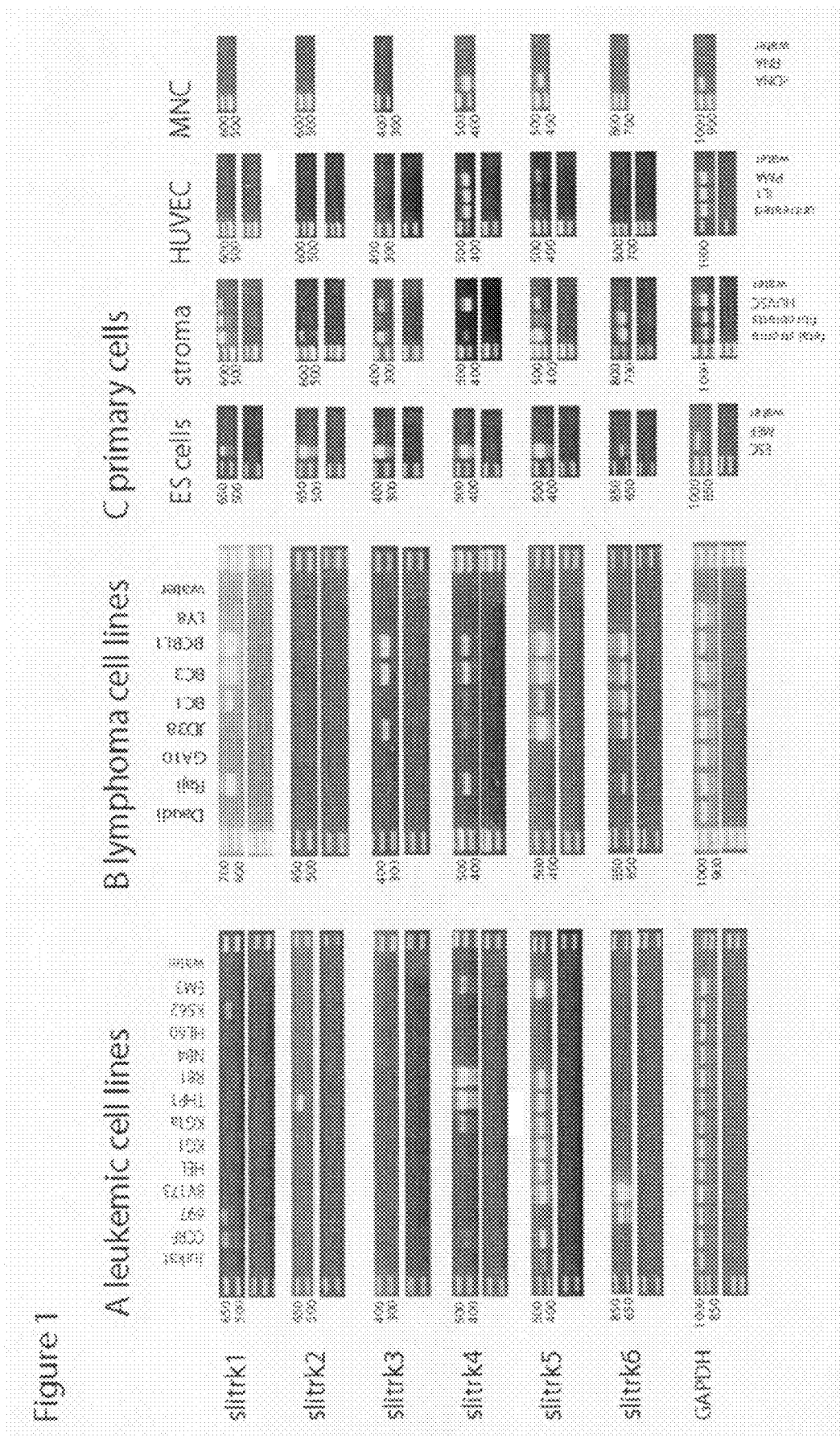
FIG. 1 shows the expression of slitrk1 to slitrk6 by primary cells and leukemic and lymphoma cell lines. RT-PCR was performed on cDNA from leukemic and lymphoma cell lines as well as primary cells. Panel A shows both myeloid and lymphoid subsets of the leukemic cells express various slitrks, and that lymphoid leukemias seem to express more slitrk1 and slitrk6, while myeloid leukemias seem to express more slitrk4 and slitrk5. It can also be seen that none of the studied leukemic cell lines express slitrk3, and that the NB4 and HL60 cells do not express any member of the slitrks. Panel B shows that lymphoma cell lines express a broader range of slitrks compared to leukemic cell lines, especially primary effusion lymphoma (PEL, BC1, BC3, BCBL1), which express five out of six slitrks; Daudi and GA-10 do not express any slitrk member. Panel C shows results of RT-PCR performed on cDNA from embryonic stem cells (ESC), fetal bone stroma (BS), adult human foreskin fibroblasts and human umbilical vein stroma cells (HUVSC), human umbilical vein endothelial cells (HUVEC) and mononuclear cells (MNC). For every cDNA sample, one RNA sample was run to control for genomic DNA contamination. Numbers on the left indicate DNA ladder fragment sizes in basepairs.

The following abbreviations are used in the specification: "AML" acute myeloid leukemia; "EPO": Erythropoietin; "ESC": embryonic stem cells; "G-CSF": Granulocyte-forming colony stimulating factor; "HFF": human foreskin fibroblasts; "HSC": hematopoietic stem cell; "HUVEC": human umbilical vein endothelial cells; "HUVSC": human umbilical vein stroma cells; "IL1": Interleukin1; "LSC": leukemic stem cells; "MEF": mouse embryonic fibroblast; "MNC": mononuclear cells; "PEL": primary effusion lymphoma; "PMA": Phorbol-myristate-acetate; "SMC": smooth muscle cells; "TPO": Thrombopoietin; "PCR": polymerase chain reaction; "qPCR": quantitative PCR. Other abbreviations may also be provided throughout the specification.

The Slitrk Family

The slitrk gene family is currently known to comprise six members, referred to as slitrk1, slitrk2, slitrk3, slitrk4, slitrk5 and slitrk6, which encode the, slitrk1, slitrk2, slitrk3, slitrk4, slitrk5 and slitrk6 proteins, respectively. In the present application, italicized names, such as slitrk1, are generally used to refer to slitrk genes or other nucleotide sequences (such as gene fragments, cDNAs, mRNAs and the like), whereas non-italicized names, such as slitrk1, are used to refer to slitrk proteins, polypeptides, peptides and the like. However, the use of either the italicized or non-italicized names should not be taken as limiting the recited slitrk to only to a nucleotide sequence or to only a protein. In many instances the description will apply equally to a protein and a nucleotide sequence. For example, where the specification states that a slitrk is a marker for stem cells, this should be construed as meaning that either the slitrk nucleotide sequence or the slitrk protein may be a marker for stem cells. Thus, unless the specification specifically states that the slitrk referred to is a slitrk protein or a slitrk nucleotide sequence, the term should be construed as encompassing both.

Slitrks belong to the leucine-rich repeat gene superfamily. The slitrks are single pass transmembrane proteins, which have a high degree of homology with slit family in the N-terminal extracellular domain and with the trk neurotrophin receptors in the C-terminal intracellular domain, hence assigned with the name slitrk (see Aruga J, Mikoshiba K. Identification and characterization of Slitrk, a novel neuronal transmembrane protein family controlling neurite outgrowth. Mol. Cell. Neurosci. September 2003; 24(1):117-129). Slitrks are highly conserved through evolution, with the human slitrks being 89-97% homologous to murine slitrks (See Aruga J, Yokota N, Mikoshiba K. "Aruga et al." Human slitrk family genes: genomic organization and expression profiling in normal brain and brain tumor tissue. Gene. Oct. 2 2003; 315:87-94). Aruga and Mikoshiba described the expression pattern of these genes in the developing brain and spinal cord as well as their involvement in controlling neurite migration and axonal guidance. Furthermore, sequence variants in the slitrk1 gene have been associated with Tourette's syndrome (see Abelson J F, Kwan K Y, O'Roak B J, et al. Sequence variants in slitrk1 are associated with Tourette's syndrome. Science. Oct. 14 2005; 310(5746):317-320). Slitrk 5 has also been identified previously as a potential marker of hematopoietic stem cells (see U.S. Pat. No. 6,670,123, the contents of which are hereby incorporated by reference).

The present invention involves all six of the currently known slitrk family members, namely slitrk1, slitrk2, slitrk3, slitrk4, slitrk5 and slitrk6. For example, all six slitrk family members are expressed in undifferentiated multipotent embryonic and fetal stem and progenitor cells and in lymphomas. In certain embodiments, the invention is directed to specific members of the slitrk family. For example, in certain embodiments the present invention is directed to leukemia cells that express only five slitrk family members, namely slitrk1, slitrk2, slitrk4, slitrk5 and slitrk6. In other embodiments, the present invention is directed to leukemias that express more slitrk1 and slitrk6 than the other slitrks, or that express predominantly slitrk1 and slitrk6, such as lymphoblastic leukemia cells. In other embodiments, the present invention is directed to stem or progenitor cells or leukemia cells that express more slitrk4 and slitrk5 than the other slitrks, or that express predominantly slitrk4 and slitrk5, such as myeloid leukemia cells and hematopoietic stem and progenitor cells and mononuclear cells. In other embodiments, the present invention is directed to cells that express more slitrk4 than the other slitrks, or that express predominantly slitrk4, such as CD14+ monocytes. In further embodiments, the present invention is directed to cells that express more slitrk5 than the other slitrks, or that express predominantly slitrk5, such as CD8+ CD4+ T-cells. In yet other embodiments, the present invention is directed to endothelial cells that express predominantly slitrk4 and slitrk5.

The nucleotide and amino acid sequences of various slitrk genes and proteins are known in the art (see for example Aruga et al., the contents of which are hereby incorporated by reference). The present invention encompasses, inter alia, slitrk proteins having the nucleotide and/or amino acid sequences known in the art, and also all homologues, orthologs, derivatives, variants, fragments, polymorphs, or mutant versions thereof. For example, the present invention encompasses, inter alia, the use of any mammalian slitrk ortholog as a stem cell or cancer cell marker, including, but not limited to, primate, rodent, ovine, bovine, porcine, equine, feline and canine slitrk orthologs. The present invention also encompasses different polymorphs of slitrks. For example, different individuals from within a given species are likely to contain varying sequences, for example as the result of the presence of single-nucleotide polymorphisms (SNPs).

The terms "protein" and "peptide", as used herein, refer to polymeric chain(s) of amino acids. Although the term "peptide" is generally used to refer to relatively short polymeric chains of amino acids, and the term "protein" is used to refer to longer polymeric chain of amino acids, there is some overlap in terms of molecules that can be considered proteins and those that can considered peptides. Thus, the terms "protein" and "peptide" may be used interchangeably herein, and when such terms are used they are not intended to limit in anyway the length of the polymeric chain of amino acids referred to. Unless otherwise stated, the terms "slitrk protein" and "slitrk peptide" should be construed as encompassing all fragments, derivatives, variants, homologues, and mimetics of the specific slitrk proteins mentioned, and may comprise naturally occurring amino acids or synthetic amino acids.

Subjects

As used herein, the term "subject" is used to refer to any animal. In preferred embodiments, the subject is a mammal selected from the group consisting of primates (such as humans and monkeys), rodents, (such as mice, rats and rabbits), ovine species (such as sheep and goats), bovine species (such as cows), porcine species, equine species, feline species and canine species. In a most preferred embodiment, the subject is a human.

Agents

In certain embodiments, the present invention is directed to agents that bind to a slitrk protein, such as the slitrk 1, 2, 3, 4, 5, or 6 proteins. The agent may be any molecule that has the property of binding to a slitrk protein, without limitation, and, for certain embodiments, such as cell separation and purification embodiments, is preferably an agent that binds to the extracellular domain of a slitrk protein. Thus, the term "agent" includes, but is not limited to, small molecule drugs, peptides, proteins, peptidomimetic molecules and antibodies. The term agent also includes any slitrk-binding molecule that is labeled with a detectable moiety, such as a histological stain, an enzyme substrate, a fluorescent moiety, a magnetic moiety or a radio-labeled moiety. Such "labeled" agents are particularly useful for embodiments involving isolation or purification of slitrk-positive cells, or detection of slitrk-positive cells.

In embodiments where the agent is an antibody, the antibody may be any suitable antibody, such as any polyclonal or monoclonal antibody that binds to slitrk. In certain preferred embodiments, such as cell separation and purification embodiments, the antibody is preferably an antibody that binds to the extracellular domain of slitrk. The term antibody, as used herein also refers to any intact antibody, any antibody fragment that retains the ability to bind to slitrk, and any antibody derivative that retains the ability to bind to slitrk, including, but not limited to, humanized antibody derivatives.

In certain embodiments, the agent may be immobilized on a solid support, such as a column, beads, a resin or a microtiter plate. One of skill in the art can readily select a suitable solid support and attach an agent to such a solid support.

Methods for Enriching, Isolating, or Purifying Slitrk-Positive Cells

The present invention provides methods for separating, enriching, isolating or purifying slitrk-positive cells from a mixed population of cells, comprising obtaining a mixed population of cells, contacting the mixed population of cells with an agent that binds to a slitrk protein, and separating the subpopulation of cells that are bound by the agent from the subpopulation of cells that are not bound by the agent, wherein the subpopulation of cells that are bound by the agent is enriched for slitrk-positive cells, such as stem or progenitor cells, or cancer cells, or endothelial cells.

The mixed population of cells can be any source of cells from which it is desired to obtain slitrk-positive cells, including but not limited to a tissue biopsy from a subject, a dissociated cell suspension derived from a tissue biopsy, or a population of cells that have been grown in culture. For example, in one embodiment, the mixed cell population may contain cultured slitrk-positive stem or progenitor cells mixed with other cells, such as slitrk-positive hematopoietic stem cells mixed with non-stem cells from the hematopoietic system. The mixed population of cells may also contain slitrk-positive endothelial cells, or slitrk-positive cancer cells.

The agent used can be any agent that binds to a slitrk, as described above. In preferred embodiments, the agent is an antibody that binds to a slitrk. In more preferred embodiment, the agent is an antibody that binds to the extracellular domain of a slitrk protein.

There are many cell separation techniques known in the art, and any such technique may be used. For example magnetic cell separation techniques may be used if the agent is labeled with an iron-containing moiety. Cells may also be passed over a solid support that has been conjugated to an agent that binds to a slitrk, such that the slitrk-positive cells will be selectively retained on the solid support. Cells may also be separated by density gradient methods, particularly if the agent selected significantly increases the density of the slitrk-positive cells to which it binds. In a preferred embodiment, the agent is a fluorescently labeled antibody against a slitrk protein, and the slitrk-positive stem or progenitor cells are separated from the other cells using fluorescence activated cell sorting (FACs). One of skill in the art can readily perform such cell sorting methods without undue experimentation.

Methods for Detecting Slitrk-Positive Cells

The present invention provides methods for detecting slitrk-positive cells in a tissue, tissue sample or cell population, wherein the method comprises obtaining a tissue, tissue sample or cell population, contacting the tissue, tissue sample or cell population with an agent that binds to a slitrk protein, and determining whether the agent has bound to the tissue, tissue sample or cell population, wherein binding indicates the presence of stem or progenitor cells and the absence of binding indicates the absence of stem or progenitor cells. In certain embodiments, the amount of agent bound to the tissue, tissue sample or cell population is quantified, wherein the greater the amount of agent that is bound, the greater the number of slitrk-positive cells the tissue, tissue sample or cell population contains. The binding of the agent may also be localized such that specific tissue regions and specific cells types that are positive for slitrk can be identified.

The agent used can be any agent that binds to a slitrk protein, as described above. In preferred embodiments, the agent is an antibody that binds to slitrk. In more preferred embodiment, the agent is an antibody that binds to the extracellular domain of slitrk. More preferably still, the antibody is labeled with a detectable moiety, such as a histological stain, an enzyme substrate, a fluorescent moiety, a magnetic moiety or a radiolabeled moiety.

There are many cell and protein detection techniques known in the art, and any such techniques may be used. For example, slitrk-positive cells may be detected by performing immunostaining of tissues, tissue samples, or cells, and detecting the presence of bound antibody. For example, this can be performed using a fluorescently labeled antibody to perform the immunostaining and then using fluorescence microscopy, such as confocal fluorescence microscopy, to detect the labeled cells. Cells labeled with fluorescent antibodies can also be detected by other techniques, including, but not limited to, flow cytometry techniques. Importantly, the agent used may comprise two or more "layers" of agents. For example the agent may consist of a primary antibody that binds to slitrk but that is not itself labeled with a detectable moiety, and a secondary antibody that binds the primary antibody wherein the secondary antibody is labeled with a detectable moiety. Such multi-layered detection techniques and agents are advantageous in that they could enhance the ability to detect low levels of slitrk protein by amplifying the amount of detectable moiety that can bind (indirectly) to the slitrk protein. Any suitable method and any suitable detectable moiety can be used for such immunostaining-based detection methods. Other types of immuno-based detection methods that may be employed include, but are not limited to, Western blotting and immunoprecipitation.

In certain embodiments, the present invention provides methods for detecting slitrk-positive cells in a tissue, tissue sample or cell population by determining whether the tissue, tissue sample or cell contains slitrk mRNA. The greater the amount of slitrk mRNA detected, the greater the number of slitrk-positive stem cells there are likely to be in the tissue, tissue sample or cell sample. There are many suitable techniques known in the art for detection of specific mRNAs and any such method can be used in accordance with the present invention. For example, slitrk mRNA may be detected by RT PCR, in situ hybridization, Northern blotting and RNAase protection, amongst other methods.

Such methods involve the use of primers and/or probes specific for slitrk. These primers and/or probes may be any nucleotide sequence that binds to a slitrk mRNA or cDNA. The primers or probes should be of sufficient length to anneal to or hybridize with (i.e. form a duplex with) the slitrk mRNA or cDNA. Such primers and/or probes may comprise about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and up to about 20, 25, 30, 35, 40, 45, 50, 55, 60, 65, 70, 75, 80, 85, 90, 95 or 100 consecutive nucleotides. In embodiments involving the detection of slitrk in a human tissue sample, it is preferred that the primers or probes comprise a string of consecutive nucleotides that are complementary to a human slitrk mRNA or cDNA. Examples of suitable primers for PCR are provided in Example 2.

The primers or probes may be labeled with any suitable molecule and/or label known in the art, including, but not limited to, fluorescent tags suitable for use in Real Time PCR amplification, for example TaqManTM, cybergreen, TAMRA and/or FAM probes. The primers or probes may also comprise other detectable non-isotopic labels, such as chemiluminescent molecules, enzymes, cofactors, enzyme substrates or haptens. The primers and/or probes may also be labeled with radioisotopes, such as by incorporation into the primer or probe of a radiolabeled nucleotide, such as a 32P dNTP.

In preferred embodiments, the hybridization or annealing conditions used are stringent conditions, such that slitrk mRNAs or cDNAs are detected specifically with minimal background from other mRNAs or cDNAs. As used herein, the phrase "stringent conditions" refers to conditions under which a probe, primer or oligonucleotide will hybridize to slitrk mRNAs or cDNAs, and can also hybridize to variant sequences, including allelic or splice variant sequences, orthologs, paralogs, and the like. The precise conditions for stringent hybridization/annealing conditions are typically sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

One of skill in the art can readily select suitable primers or probes for the detection of slitrk mRNA or cDNA, and can readily use these primers or probes in conjunction with any of the known techniques for mRNA or cDNA detection known in the art. For example, suitable methods are disclosed in Sambrook et al. (2001) Molecular Cloning: A Laboratory Manual, 3rd Ed., Cold Spring Harbor Laboratory, Cold Spring Harbor, N.Y. ("Sambrook") and Haymes et al., "Nucleic Acid Hybridization: A Practical Approach", IRL Press, Washington, D.C. (1985), both of which references are incorporated herein by reference.

Methods of Culturing and Cryopreserving Slitrk-Positive Cells

The slitrk-positive cells of the invention can be cultured using any suitable method known in the art. For example, slitrk-positive hematopoietic stem cells can be cultured by any of the methods known in the art for the culture of hematopoietic stem cells. Similarly, slitrk-positive embryonic stem cells can be cultured by any of the methods known in the art for the culture of embryonic stem cells. The slitrk-positive cells of the invention can also be cryogenically frozen and stored for use at a later time. This is particularly advantageous for the autologous transplantation methods provided herein. Methods of cryogenically freezing and storing cultured cells are well known in the art, and any such method can be used. See, for example, Culture of Animal Cells: A Manual of Basic Technique, by R. Ian Freshney, Wiley-Liss, 5th Edition (Jul. 29, 2005), Chapter 19 "Cryopreservation". Methods of freezing hematopoietic stem cells and embryonic stem cells are also known in the art.

Purified Slitrk-Positive Cells and Compositions Comprising Slitrk-Positive Cells In certain embodiments, the present invention provides purified preparations of slitrk-positive cells, such as those obtained using the cell separation methods described above. As used herein the term "purified" does not mean that there can not be any non-slitrk-positive cells present in the preparation. Instead the term "purified" means substantially free of non-slitrk-positive stem or progenitor cells, or pure enough to be safe for administration to a living subject, or pure enough to satisfy the requirements for safety of biologic products laid down by the FDA.

In one preferred embodiment, the invention provides a purified preparation of embryonic stem cells. In another one preferred embodiment, the invention provides a purified preparation of hematopoietic stem cells. In yet another embodiment, the invention provides a purified preparation of endothelial cells.

Several embodiments of the invention involve therapeutic compositions comprising purified slitrk-positive cells. These compositions comprise a purified preparation slitrk-positive cells, as described above, and a carrier suitable for administration to living subjects, such as humans. In a preferred embodiment the carrier is a physiological saline solution. Other therapeutically acceptable agents may be included if desired. One of skill in the art can readily select suitable agents to be included in the therapeutic compositions depending on the desired outcome.

Methods of Treatment Using Slitrk-Positive Cells

The present invention also provides various methods of treatment. For example, the present invention provides methods of treatment comprising administering slitrk-positive cells to a subject in need thereof. In a preferred embodiment, this method comprises obtaining a tissue sample, isolating or purifying the slitrk-positive cells from the tissue sample in vitro, and then administering the slitrk-positive cells to the subject. One of skill in the art can readily perform such methods by preparing a therapeutic composition containing slitrk-positive stem cells, as described above, and administering the therapeutic composition to a suitable subject, such as a human patient, using the administration methods described below.

In preferred embodiments, the present invention provides methods for autologous transplantation, wherein a tissue sample is obtained from a subject, the slitrk-positive cells from the tissue sample are purified and optionally expanded in vitro, for example using the methods described above, and then the slitrk-positive stem or progenitor cells are administered to the same subject from which the tissue sample was obtained, for example using the administration methods described below. Such autologous transplantation methods are particularly useful for subjects in need of chemotherapy or radiation therapy, where a tissue sample may be removed from the subject before therapy, and the slitrk-positive cells may be administered to the subject after therapy.

In one preferred embodiment of the present invention, the slitrk-positive cells are hematopoietic stem or progenitor cells. Methods of treatment using slitrk-positive hematopoietic stem or progenitor cells may be particularly useful when the subject is suffering from, or is at risk of developing, a disease, disorder, or condition affecting the hematopoietic system, such as aplastic anemia or cancer, and also in patients undergoing chemotherapy or radiation therapy.

The present invention encompasses methods of treatment performed by administering differentiated cells, or partially differentiated or committed cells, that have been derived from slitrk-positive stem or progenitor cells in vitro, such as from slitrk-positive embryonic stem cells. For example, the present invention encompasses methods of treatment performed by administering differentiated, or partially differentiated cells such as nerve cells, cardiac cells, muscle cells and other cell types that have been derived in vitro by differentiating slitrk-positive embryonic stem cells or other slitrk-positive stem or progenitor cells.

One of skill in the art can readily perform such treatment methods by preparing a therapeutic composition containing slitrk-positive stem cells, as described above, and administering the therapeutic composition to a suitable subject, such as a human patient, using the administration methods described below.

Administration of Slitrk-Positive Cells to Subjects

Several of the embodiments of the invention involve administration of slitrk-positive cells, or differentiated cells derived from slitrk-positive cells, to subjects. The cells may be administered to subjects using any suitable means known in the art. For example, the cells may be administered by injection or infusion into the blood stream at a location peripheral to the site where the cells are needed, or by injection or infusion into the blood stream in the vicinity of the region where the cells are needed, or by direct infusion or injection into tissue, either at the site where the cells are needed, or in the vicinity of the site where the cells are needed, or at a peripheral location. In the case of slitrk-positive hematopoietic stem or progenitor cells, it is preferred that the cells are administered into the blood stream because hematopoietic stem cells have the ability to home to the bone marrow. However, the cells may also be administered directly to the bone marrow or to other sites of hematopoiesis in the body. In the case of differentiated cells derived from slitrk-positive stem and progenitor cells, it is preferred that the cells are administered directly into the site where those differentiated cells normally reside, such as the brain for certain neurons, the heart for cardiac cells, or the skeletal muscle for skeletal muscle cells. The cells may be administered in a single dose, or in multiple doses. The skilled artisan will be able to select a suitable method of administration according to the desired use.

Methods of Drug Targeting

In certain embodiments, the present invention provides a method of targeting a therapeutic agent to a slitrk-positive cell in a subject by conjugating the therapeutic agent to an agent that binds to a slitrk protein and administering the conjugated agent to the subject. Such methods can be used to target therapeutic agents, such as drugs, to any slitrk-positive cells, such as slitrk-positive hematopoietic cells. In preferred embodiments, the slitrk-binding agent binds to the extracellular domain of a slitrk protein.

For example, therapeutic agents that may be targeted to slitrk-positive cells include, but are not limited to, cytotoxic drugs, other toxins, radionuclides. Agents that bind to a slitrk protein include antibodies, preferably monoclonal antibodies, more preferably still humanized monoclonal antibodies. Such conjugates would be particularly useful in situations where the slitrk-positive cells are slitrk-positive cancer cells, or other slitrk-positive cells that are over-proliferative. In preferred embodiments, the therapeutic agents are conjugated to an antibody that binds to slitrk, preferably an antibody that binds to the extracellular domain of slitrk, and preferably a humanized monoclonal antibody. Methods of conjugating therapeutic agents to antibodies are known in the art, and any such method can be used.

Slitrks as Drug Targets

It is possible that slitrk, and any potential ligands of slitrk, may be functionally involved in stem and progenitor cell processes or cancer cell processes such as maintaining a de-differentiated state, maintaining proliferation, and the like. Agents that modulate the function of a slitrk protein or its putative ligand may therefore be useful. Thus, in one aspect, the present invention is directed to agents that modulate the function of slitrk or its ligand(s) and to methods of identifying such agents. Such agents may be useful, inter alia, as anti-leukemia or lymphoma drugs, or as agents for inhibiting over-proliferation of stem or progenitor cells, or as agents for maintaining stem cells in culture, or as agents for facilitating differentiation of stem cells into differentiated cells types. Such agents may be useful in vitro as well as in vivo.

Methods for screening for agents or drugs that bind to and/or affect the function of a drug target are well known and any suitable method may be used. For example, a suitable method may comprise providing one or more slitrk proteins, contacting the one or more slitrk proteins with a library of agents, identifying at least one agent from the library that binds to at least one of the slitrk proteins, and testing the slitrk-binding molecules to identify agents that have the desired activity, such as cell killing activity, proliferation inhibitory activity, differentiation stimulation activity, and the like.

Leukemia and Lymphoma

The present invention provides methods involving cancer cells, such as leukemia and lymphoma cells. These methods are based on the discovery that slitrks are markers of leukemia and lymphoma cells. All of the embodiments described herein can be applied to slitrk-positive leukemia and lymphoma cells.

For example, the methods of the present invention may be applied to various types of leukemias including both chronic and acute leukemias, and both lymphoblastic and myeloid leukemias, such as acute lymphoblastic leukemias (ALLs), chronic lymphoblastic leukemias (CLLs), acute myeloid leukemias (AMLs) and chronic myeloid leukemias (CMLs). It is possible that the methods of the invention may also be applied to certain other types of leukemias such as hairy-cell leukemias.

The methods of the present invention may also be applied to various types of lymphomas, including, but not limited to, B cell lymphomas, T cell lymphomas, Hodgkins lymphoma non-Hodgkins lymphoma, small lymphocytic lymphoma, lymphoplasmacytic lymphoma/Waldenström macroglobulinemia, splenic marginal zone lymphoma, extranodal marginal zone B cell lymphoma (MALT lymphoma), nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, lymphomatoid granulomatosis, extranodal NK/T cell lymphoma, nasal type, enteropathy-type T cell lymphomam hepatosplenic T cell lymphoma, blastic NK cell lymphoma, primary cutaneous anaplastic large cell lymphoma, angioimmunoblastic T cell lymphoma, peripheral T cell lymphoma, anaplastic large cell lymphoma, and nodular lymphocyte-predominant Hodgkin lymphoma.

In a preferred embodiment, the methods of the present invention may be applied to primary effusion lymphomas (or PELs). PEL is a malignancy of B cells that is caused by Kaposi's sarcoma-associated herpesvirus (KSHV), also known as human herpesvirus 8 (HHV-8). In about 80% of cases, the lymphoma cells are also infected with Epstein Barr virus (EBV). PEL is unusual in that the majority of cases arise in body cavities, such as the pleural space or the pericardium. Another name for PEL is "body cavity lymphoma". It was recognized as a unique type of lymphoma only after the discovery of KSHV in 1994.

Methods of Detecting Leukemia and Lymphoma Cells

The slitrk detection methods described above can be used for detection of slitrk-positive leukemia and lymphoma cells. Such methods may be particularly useful for the diagnosis of leukemias and lymphomas, such as in human patients.

In one embodiment, the present invention provides a method of detecting leukemia or lymphoma cells, comprising contacting a tissue, tissue sample or cell population with an agent that binds to a slitrk protein and determining whether the agent has bound to the tissue, tissue sample or cell population, wherein binding of agent indicates the presence of leukemia or lymphoma cells.

In other embodiments, the present invention provides methods for detecting leukemia or lymphoma cells, comprising obtaining a tissue, a tissue sample or a cell population, and determining whether the tissue, the tissue sample or the cells contain slitrk mRNA, wherein the presence of slitrk mRNA indicates the presence of leukemia and lymphoma cells.

The present invention also provides methods for determining whether a subject is likely to develop a leukemia or lymphoma by determining whether a tissue, tissue sample or cell population from the subject contains one or more slitrk-positive cells. It is believed that the presence of such cells may provide an early prognostic marker, and thus be useful for detecting cancers, or subjects likely to develop leukemias or lymphomas, at an early stage, allowing appropriate preventative or therapeutic regimens to be initiated early.

Method of Removing Slitrk-Positive Cells from Tissue for Transplantation

Stem cell transplants are often used for the treatment of cancer patients, such as leukemia patients. For example, bone marrow ablation using high doses of chemotherapy and/or radiation therapy, followed by infusion of stem cells from a donor bone marrow sample or autologous bone marrow sample, is now routinely performed in leukemia patients. Leukaphoresis, also known as a peripheral blood stem cell transplant, is also used. In leukaphoresis the patient's blood is passed through a machine that removes the stem cells and then returns the blood to the patient. Leukaphoresis usually takes 3 or 4 hours to complete. The stem cells may or may not be treated with drugs to kill any cancer cells. The stem cells then are stored until they are transplanted back into the patient. With both of these methods, it is desirable to kill and/or remove any contaminating cancer cells before transplantation. In one aspect, the present invention provides methods for removing slitrk-positive leukemia cells from cells and tissues to be used for transplantation. For example, the slitrk-positive leukemia cells can be separated and removed from the bone marrow or blood sample using the cell separation methods described above. Such methods may be performed in conjunction with negative selection for other cancer or leukemia cell markers also.

Methods of Targeting Drugs to Leukemia or Lymphoma Cells

In one embodiment, the present invention is directed to methods for targeting drugs to leukemia and lymphoma cells for the treatment of leukemias and lymphomas. The drug targeting methods described above can be used to target drugs to slitrk-positive leukemia and lymphoma cells. For example, agents such as chemotherapeutic drugs, radionuclide drugs, or other toxic agents can be targeted to slitrk-positive leukemia and lymphoma cells, thereby killing the cancer cells but not the surrounding non-cancerous tissue. Examples of drugs that could be targeted to slitrk-positive cancer cells using the methods of the invention include, but are not limited to daunorubicin, cytarabine (ara-C), idarubicin, thioguanine, etoposide, mitoxantrone, interferon-alpha, hydroxyurea (Hydrea®), busulfan (Myleran®), imatinib mesylate (Gleevec™), dasatinib (Sprycel™), prednisone, vincristine, paclitaxel (Taxol®) and methotrexate. In addition, the drug-targeting methods of the present invention may be used in conjunction with other drugs and/or treatment methods known and used in the art for treatment of leukemias.

Primary effusion lymphomas are unusually resistant to cancer chemotherapy drugs that are active against other lymphomas, and generally have a very poor prognosis. The drug-targeting methods of the invention could be used to specifically target existing or new cancer drugs to primary effusion lymphoma cells, thereby increasing their efficacy.

Slitrks as Targets for Development of New Drugs

In another embodiment, the present invention is directed to methods of identifying agents that could be useful for the treatment of leukemias and lymphomas by identifying and/or screening for agents that bind to slitrks, or agents that bind to slitrk-expressing cells, and determining if those agents are useful for killing slitrk-positive cells or inhibiting the proliferation of slitrk-positive cells. Such agents may be, for example, small molecule drugs, protein or peptide drugs, or antibodies, such as monoclonal antibodies or humanized monoclonal antibodies. Methods of screening for drugs or agents that bind to a particular protein, and that have a certain desired effect such as killing cells or inhibiting the proliferation of cells, are well known in the art and any such methods could be used. For example, a suitable method for identifying agents having anti-leukemia or anti-lymphoma activity may comprise providing one or more slitrk proteins, contacting the one or more slitrk proteins with a library of agents, identifying at least one agent from the library that binds to at least one of the slitrk proteins, and testing the slitrk-binding agents to identify molecules that kill, or inhibit the proliferation of, leukemia or lymphoma cells.

As stated above, primary effusion lymphomas are unusually resistant to cancer chemotherapy drugs that are active against other lymphomas, and generally have a very poor prognosis. Thus, slitrks may provide a promising drug target for the development of drugs against primary effusion lymphomas.

These and other embodiments of the invention are further described in the following non-limiting examples.

EXAMPLES

In the following examples, the numbers in parentheses refer to the numbered publications provided in the reference list at the end of each Example.

Example 1

In a search for new markers of primitive hematopoietic cells, we discovered that members of a recently described family of six putative transmembrane receptors called slitrk1-slitrk6 are expressed on leukemic and lymphoma cells as well as hematopoietic stem cells. Slitrks belong to the leucine-rich repeat superfamily; they are single pass transmembrane proteins, with homology to the slit family in the N-terminal extracellular domain and with the trk neurotrophin receptors in the C-terminal intracellular domain—hence assigned with the name slitrk (1). Slitrks are highly conserved through evolution, with the human slitrks being 89-97% homologous to murine slitrks (2). Aruga and Mikoshiba described the expression pattern of these genes in the developing brain and spinal cord as well as their involvement in controlling neurite migration and axonal guidance (1). We previously described the differential expression of slitrk5 (referred to as KIAA0918) on CD34+ leukemic cell lines (3). These data led to the hypothesis that they were relevant for hematopoiesis and possibly leukemogenesis. Results from the present study revealed that of 13 leukemic cell lines all four acute lymphoblastic leukemia (ALL), five out of seven acute myelogenous leukemia (AML) and all of two chronic myelogenous leukemia (CML) cell lines express one or more members of the slitrk family (FIG. 1A). Comparison of the two closely related cell lines KG1 and KG1a revealed a specific expression pattern for slitrk4: it is expressed only by the undifferentiated variant KG1a, but not by the parental KG1 cell line. Only two leukemic cell lines do not express any of the slitrks, namely the myeloid leukemic cell lines NB4 and HL60. There also seemed to be a trend towards lymphoblastic leukemic cells expressing more slitrk1 and slitrk6, with myeloid leukemic cells expressing more slitrk4 and slitrk5. The lymphoma cell lines showed a distinct expression pattern, for example two cell lines (Daudi and GA10) showed no expression of any of the slitrks, while three cell lines (BC1, BC3 and BCBL1) showed expression of five out of six slitrks (FIG. 1B). Most notably, the latter cell lines are all primary effusion lymphomas (PEL), a distinct clinical entity of diffuse body cavity-located lymphomas with no single tumor mass as well as a poorer prognosis in comparison to other lymphomas (4,5).

In order to assess expression patterns of slitrks by primary cells, we studied the expression of slitrk genes on human mononuclear cells (MNC) isolated from peripheral blood, human umbilical vein endothelial cells (HUVEC), human fetal bone stroma (BS), human foreskin fibroblast (HFF) and human umbilical vein stroma cells (HUVSC) and human Miz-hES5 embryonic stem cells (ESC) by RT-PCR. All six members of the slitrk family were expressed by human ESCs (FIG. 1C). To exclude the possibility of contamination by mouse embryonic fibroblast (MEF) feeder cells, we demonstrated that human slitrk members were not expressed by MEF using the same set of primers. Human fetal bone stroma showed a pattern similar to that of ESC, as did HUVSC, with all six members of slitrks being expressed on these cells. However, adult HFF showed a different and more specific pattern, expressing only slitrk1 and slitrk6 (FIG. 1A). This suggests that embryonic and fetal tissues maintain the expression of slitrks during development, in contrast to terminally differentiated cells.

Figure 2:
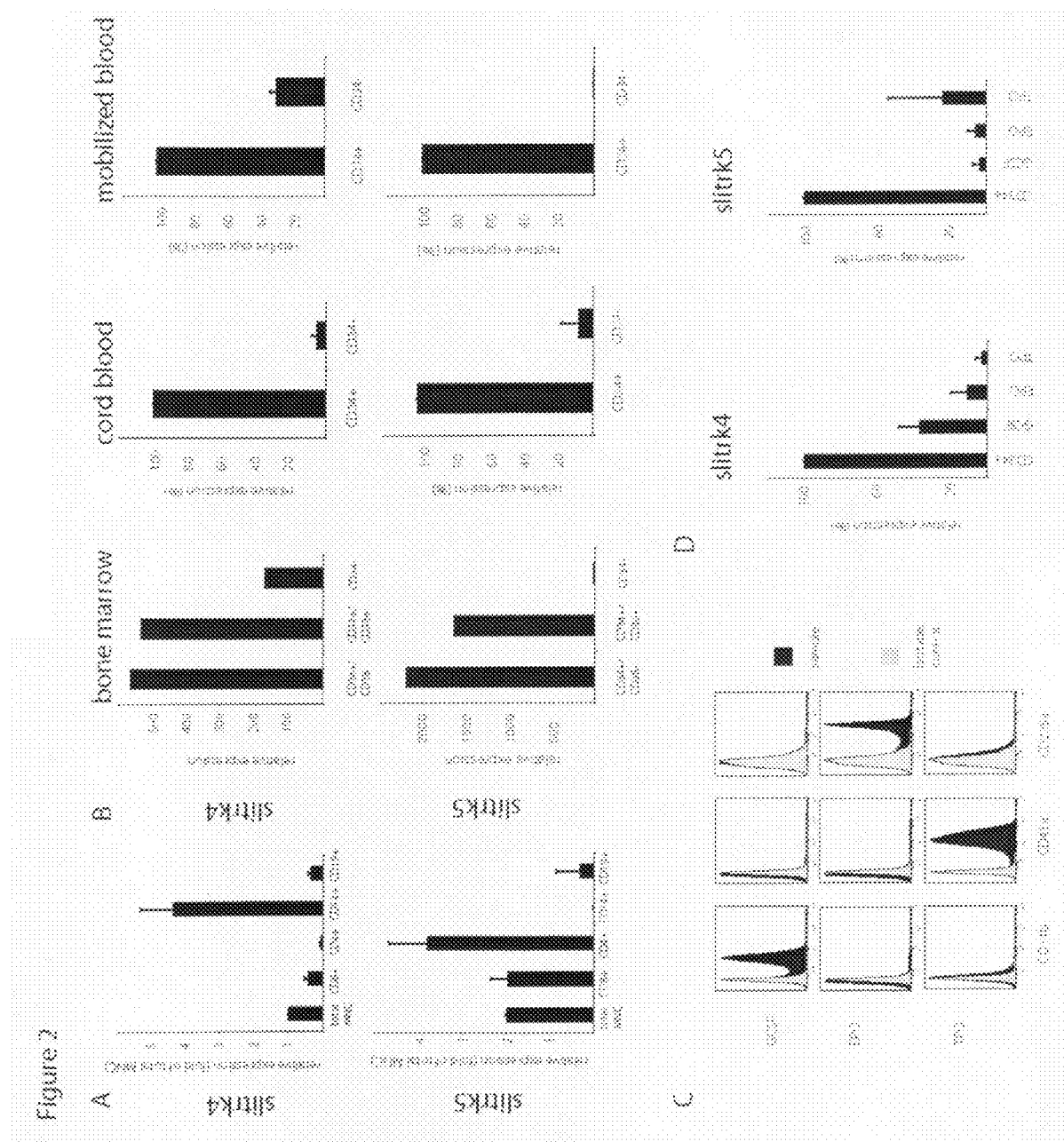
FIG. 2 shows expression of slitrk4 and slitrk5 by human primary cells and hematopoietic stem/progenitor cells and the effect on lineage commitment. Panel A shows cDNA from total mononuclear cells (MNC), and fractions thereof, analyzed by quantitative PCR (qPCR, Taqman) for expression of slitrk4 and slitrk5: slitrk4 appears to be expressed mainly in the monocytic compartment (CD14+), while slitrk5 is primarily expressed by T-cells (CD8+ and CD4+); relative expression is given in manifolds of expression of total MNC (average), error bars represent standard deviation (n=3 independent measurements). Panel B shows results from cells isolated using cell sorting (bone marrow) or magnetic isolation (cord blood and mobilized blood). qPCR was performed on cDNA from the respective cells. It can be seen that the relative expression of slitrk4 and slitrk5 in hematopoietic stem and progenitor cells isolated from adult bone marrow, cord blood or mobilized peripheral blood is higher in the immature CD34+ than in the CD34− populations. Representative results from bone marrow are also shown. In cord blood and mobilized blood expression of slitrk4 or slitrk5 on CD34− cells is represented as the percent of the CD34+ population (average). The error bars represent the standard deviation (n=3 independent experiments). Panels C and D show data from CD34+ hematopoietic cells that were differentiated in vitro. Quantitative PCR (Taqman) was performed on cDNA from the respective cells. Panel C shows the analysis of surface markers CD11b, CD41a and CD235a by flow cytometry. Panel D shows the relative expression of slitrk4 and slitrk5 by undifferentiated CD34+ cells and in vitro differentiated cells, as measured by quantitative PCR. Relative expression for each group is given as the percent of the corresponding relative expression of CD34+ cells (average). Error bars represent standard deviation (n=3 independent experiments).

Analysis of slitrk expression on vascular cells revealed a highly contrasting expression pattern to that of fibroblasts. RT-PCR analysis showed that HUVEC expressed only slitrk4 and slitrk5 (FIG. 1C). Activation of HUVEC with Interleukin1 (IL1) or Phorbol-myristate-acetate (PMA) had no major effect on the expression pattern of slitrk1-slitrk6 except for a slight increase in the expression of slitrk5. Human MNC isolated from peripheral blood of healthy donors by density gradient separation (Ficoll) express only slitrk4 and slitrk5 (FIG. 1C). This pattern of expression of slitrk4 and slitrk5 is identical to that detected on HUVECs, but different from the studied leukemic cell lines. This difference in slitrk expression between leukemic and lymphoma cell lines and normal MNC is possibly due to reactivation of slitrks during malignant transformation. Since MNC showed expression of slitrk4 and slitrk5 we studied the expression of these two genes in different fractions of MNCs (total MNC, CD8+, CD4+ CD14+ and CD 19+), using quantitative PCR (qPCR, Taqman) on a panel of commercially available cDNAs (Human Blood Fractions MTC Panel by Clontech, Mountain View, Calif.). qPCR revealed that slitrk4 is primarily expressed in the CD14+ compartment (monocytes), while slitrk5 was mainly expressed by T-cells (CD8+ and CD4+) (FIG. 2A).

The initial finding of slitrks being expressed on CD34+ leukemic cells prompted us to investigate the expression of slitrks on hematopoietic stem and progenitor cells. Hematopoietic CD34+CD38− as well as CD34+ stem and progenitor cells were sorted from human bone marrow (MoFlo High-Performance Cell Sorter, Dako Cytomation, Glostrup, Denmark) and isolated from cord blood and mobilized peripheral blood of healthy donors respectively (magnetic cell sorting, MACS Miltenyi Biotec Inc., Auburn, Calif.). qPCR analysis revealed that highly purified population of human CD34+ CD38− hematopoietic stem and progenitor cells isolated from bone marrow express slitrk4 and slitrk5, but not other members of the slitrk family. The CD34+CD38+ fraction also expressed slitrk4 and slitrk5, while the cells of the CD34− fraction express both genes at a very low level (FIG. 2B). Human CD34+ hematopoietic progenitor cells isolated from umbilical cord blood also expressed both slitrk4 and slitrk5, while the CD34− population expressed significantly lower levels of slitrk4 and slitrk5 (FIG. 2B). This pattern is reproduced in the CD34+ and CD34− populations purified from mobilized peripheral blood of healthy donors treated with Granulocyte-Colony Stimulating Factor (G-CSF) (FIG. 2B).

Since the CD34− fraction of expressed slitrk4 and slitrk5 only at a low level, we investigated the expression of these genes following cytokine-driven in vitro differentiation of human CD34+ cells. The CD34+ population purified from cord blood was selectively differentiated into myeloid/granulocytic, erythroid and megakaryocytic lineages using G-CSF, Erythropoietin (EPO) or Thrombopoietin (TPO), respectively, over 12 days. The phenotype of the differentiated cells was confirmed by flow cytometry using three lineage-specific markers, namely CD11b for the myeloid, CD41a for the megakaryocytic and CD235a for the erythroid lineage (FIG. 2C). Remarkably, although the undifferentiated cells showed robust expression of slitrk4 and slitrk5, the expression of these genes was drastically downregulated upon differentiation into the analyzed lineages. Only very low levels of slitrk4 and slitrk5 were detected on the mature CD11b+ myeloid, CD41a+ megakaryocytic or CD235a+ erythroid (FIG. 2D). These data indicate that slitrk4 and slitrk5 are predominantly expressed on immature human hematopoietic stem and progenitor cells.

HSC have been studied for their potential in reconstituting hematopoiesis (6) as well as for their promise as targets in the treatment of hematological malignancies (7). Here, we show for the first time that undifferentiated multi-potent cells, including human ESC and fetal bone stroma express all six members of the slitrk family, indicating the potential importance of slitrks for the identification of these primitive cells during developmental processes. However, the adult stem and progenitor cells, e.g. human bone marrow CD34+CD38− cells and cord blood-derived as well as mobilized CD34+ cells, express only slitrk4 and slitrk5. Our study suggests that slitrks could be involved in normal as well as malignant hematopoiesis, as indicated by the expression on leukemias, and possibly in embryonic development. Thus, slitrks may constitute a novel marker of hematopoietic stem and progenitor cells and embryonic stem cells.

References for Example 1

(1) Aruga J and Mikoshiba K: Identification and characterization of Slitrk, a novel neuronal transmembrane protein family controlling neurite outgrowth. Mol Cell Neurosci (2003): 24, 117-129.
(2) Aruga J, Yokota N and Mikoshiba K: Human slitrk family genes: genomic organization and expression profiling in normal brain and brain tumor tissue. Gene (2003): 315, 87-94.
(3) Shmelkov S V, Visser J W and Belyavsky A V: Two-dimensional gene expression fingerprinting. Anal Biochem (2001): 290, 26-35.
(4) Nador R G, Cesarman E, Chadburn A, Dawson D B, Ansari M Q, Sald J, et al.: Primary effusion lymphoma: a distinct clinicopathologic entity associated with the Kaposi's sarcoma-associated herpes virus. Blood (1996): 88, 645-656.
(5) Simonelli C, Spina M, Cinelli R, Talamini R, Tedeschi R, Gloghini A, et al.: Clinical features and outcome of primary effusion lymphoma in HIV-infected patients: a single-institution study. J Clin Oncol (2003): 21, 3948-3954.
(6) Osawa M, Hanada K, Hamada H and Nakauchi H: Long-term lymphohematopoietic reconstitution by a single CD34-low/negative hematopoietic stem cell. Science (1996): 273, 242-245.
(7) Bonnet D and Dick J E: Human acute myeloid leukemia is organized as a hierarchy that originates from a primitive hematopoietic cell. Nat Med (1997): 3, 730-737.

Example 2

A novel family of slitrk genes encodes for leucine-rich transmembrane proteins with predominant expression in neural tissues. Six members of this family have been identified, however, their function remains unclear. Using a gene fingerprinting approach, we previously detected slitrks on leukemic cells, suggesting that the expression of these genes may be more widely distributed. Here, we show that CD34+CD38− hematopoietic stem and progenitor cells derived from adult bone marrow as well as CD34+ cells isolated from cord blood and from mobilized peripheral blood express only slitrk4 and slitrk5. Remarkably, expression of slitrk 4 and slitrk5 was rapidly downregulated with in-vitro cytokine-driven lineage-specific differentiation. In addition, virtually all of the studied leukemic and lymphoma cell lines express various slitrks. We also demonstrate that all members of the slitrk family are expressed by human embryonic stem cells. Furthermore, similar to hematopoietic cells, primary endothelial cells specifically express slitrk4 and slitrk5, while adult fibroblasts express slitrk1 and slitrk6. This data suggests that slitrks constitute new differentiation markers in hematopoietic and vascular development, with slitrk4 and slitrk5 being expressed predominantly in early primitive hematopoietic stem and progenitor cells as well as in endothelial cells. As such, slitrks may play a role in modulating hemangiogenesis, neo-angiogenesis as well as malignant hematopoiesis.

Hematopoietic stem cells (HSC) and vascular progenitor cells have been studied for their potential in reconstituting hematopoiesis and vascular beds (1-3) as well as for their promise as targets in the treatment of hematological malignancies and angiogenesis-dependent diseases (4, 5). However, identification and purification of hemangiogenic stem and progenitor cells have been hampered by lack of common markers expressed by primitive endothelial and hematopoietic cells. Early hemangiogenic cells have been shown to express CD34 (6), CD133 (7) and c-Kit (8) among other markers, and the expression of these markers is down-regulated upon differentiation. The absence of lineage specific surface markers (9), or dye efflux capacity (10), has also been used for identification of hematopoietic stem cells. However, these approaches are not efficient for the identification of either bona fide self-renewing hematopoietic stem cells or vascular progenitor cells.

The family of the slitrk genes comprises six members, called slitrk1 to slitrk6. Slitrks belong to the leucine-rich repeat superfamily, they are single pass transmembrane proteins, which have a high homology with slit family in the N-terminal extracellular domain and with the trk neurotrophin receptors in the C-terminal intracellular domain, hence assigned with the name slitrk (11). Slitrks are highly conserved through evolution, with the human slitrks being 89-97% homologous to murine slitrks (12). Aruga and Mikoshiba (11) described the expression pattern of these genes in the developing brain and spinal cord as well as their involvement in controlling neurite migration and axonal guidance. Furthermore, sequence variants in the slitrk1 gene have been associated with Tourette's syndrome (13).

In search of new markers for embryonic and primitive hemangiogenic cells, we have identified a novel family of putative transmembrane receptors being expressed on primitive hematopoietic and vascular cells. Shmelkov et al showed that CD34+ leukemic cells expressed members of the slitrk family (14). The association of immature cells and expression of these novel genes led to the hypothesis that they were relevant for hematopoiesis. Here, we show for the first time that these genes are differentially expressed by human embryonic stem cells, phenotypically marked CD34+CD38− hematopoietic stem cells, CD34+ hematopoietic progenitors, vascular cells and leukemic cell lines. Most notably, slitrk4 and slitrk5 are selectively expressed only on vascular cells and hematopoietic stem/progenitor cells. Expression of slitrk4 and slitrk5 is downregulated with in vitro differentiation of CD34+ cells isolated from cord blood. This implicates slitrk4 and slitrk5 as markers of early stages of hemangiogenic differentiation.

Human embryonic stem cells 15, Miz-hES5, were cultured on mouse embryonic fibroblasts (MEF) from CF1 mice (P3) and passaged as described previously (16). The Institutional Review Board of Cornell University Medical College approved the use of Miz-hES5 and fetal tissue. Fetal bone stroma (BS) cells were isolated and cultured as described previously (17). Human foreskin fibroblasts (HFF) were isolated from human foreskin specimens and cultured in MEM, 10% fetal bovine serum (FBS), 100 µg/ml penicillin, and 100 µg/ml streptomycin. Human umbilical vein endothelial cells (HUVEC) and stroma cells (HUVSC) were isolated from umbilical cord veins with collagenase and were cultured in M199 medium containing 10% (vol/vol) FBS, 20 µg/ml endothelial cell growth factor, 50 µg/ml heparin, 100 µg/ml penicillin and 100 µg/ml streptomycin. HUVEC and HUVSC monolayers from passages 2-4 were used in these studies. HUVECs were stimulated with Interleukin1 (IL1, 10 ng/ml final concentration) and Phorbol-myristate-acetate (PMA, 100 nM final concentration) for 24 h before collection. Cell lines (Jurkat, CCRF, 697, BV173, HEL, KG1, KG1a, THP1, NB4, HL60, K562, EM3, Daudi, Raji, GA10, JD38, BC1, BC2, BCBL1, LY8) were obtained through American Type Culture Collection (ATCC, Manassas, Va.) and cultured according to ATCC guidelines. One cytogenetically normal AML cell line (designated R81), which was established in our laboratory from primary AML in an 81 year-old male, was also used. The immunophenotype of R81 AML cells in culture was CD7+, CD13+, CD33+, CD3−, CD19−, CD34−, CD117− consistent with immature myeloid blasts. R81 cells were cultured in IMDM (Cellgro Mediatech Inc., Herndon, Va.), 10% FBS, 100 µg/ml penicillin and 100 µg/ml streptomycin.

All cultured cells were cultured in a humidified incubator at 37° C. with air/5% CO2. All patient samples were obtained after informed consent in accordance with the institutional review board (IRB) of the Weill Medical College of Cornell University. Cord blood was obtained through the National Cord Blood Center at New York Presbyterian Hospital. Mononuclear cells (MNC) were isolated from bone marrow, cord blood and from peripheral blood of healthy donors using Ficoll-Paque (Amersham Biosciences, Piscataway, N.J.) according to manufacturer's protocol. CD34+ cells were isolated from MNC from cord blood, mobilized peripheral blood or human bone marrow by magnetic cell sorting according to the manufacturer's protocol using the CD34 Progenitor Cell Isolation kit (Miltenyi Biotec Inc., Auburn, Calif.). CD34+ CD38− cells were then sorted from the CD34+ population from bone marrow. The isolated cells were stained as described in "Flow cytometry" with the following antibodies: human CD34 FITC (BD Biosciences) and human CD38 PE (BD Biosciences). Cells were then sorted using a MoFlo High-Performance Cell Sorter (Dako Cytomation, Glostrup, Denmark).

Differentiation Assay. CD34+ cells were isolated from human umbilical cord blood and were incubated with various cytokines to induce lineage-specific differentiation. To induce lineage specific differentiation, CD34+ cells were cultured in ex-vivo (Cambrex, East Rutherford, N.J.), 10% FBS, 100 µg/ml penicillin and 100 µg/ml streptomycin, for 12 days with granulocyte-forming colony stimulating factor (G-CSF, 1000 U/ml; Amgen Inc., Thousand Oaks, Calif.), erythropoietin (EPO, 6 U/ml; Amgen Inc.) or thrombopoietin (TPO, 100 ng/ml; Amgen Inc.) respectively. Kit-ligand (50 ng/ml; Peprotech Inc., Rocky Hill, N.J.) was added to the samples on day 1 and 3. After 12 days RNA was extracted from each fraction separately, after prior analysis of an aliquot by flow cytometry.

Total RNA was extracted from $1\times10^7$ cells using Trizol (Invitrogen Corp., Carlsbad, Calif.) according to the manufacturers protocol, followed b DNase I treatment (Promega, Madison, Wis.). RNA from CD34+ and CD34− cell populations and populations differentiated from the CD34+ population was extracted using the RNaqueous Micro kit (Ambion, Austin, Tex.), including optional DNase I treatment.

cDNA synthesis was performed using Superscript II (Invitrogen Corp) according to the manufacturers instructions. All samples used for quantitative PCR (qPCR) were treated with DNase I (Roche, Indianapolis, Ind.) immediately prior to cDNA synthesis. PCR was performed using Advantage2 Polymerase (BD Biosciences, Palo Alto, Calif.) and the following primers. slitrk1: forward primer (Frw): 5'-TCCTCAT-TCTCAACAACAAC-3' (SEQ ID NO: 1); reverse primer (Rev): 5'-GCCAGTAGGAAGAGTCACAG-3' (SEQ ID NO: 2) (amplicon length: 597bp; annealing temperature: 62° C.; number of cycles: 40; elongation time: 60s); slitrk2: Frw: 5'-GACAACCTTCTGCTTTCACT-3' (SEQ ID NO: 3); rev: 5'-GGCAGTTTACATTCAGACCA (SEQ ID NO: 4) (580bp; 60° C.; 35; 60s); slitrk3: Frw: 5'-CCTGGAGAAGACAA-CATACA-3' (SEQ ID NO: 5); Rev: 5'-ATGGCACAGT-CAAAGTCTCA-3' (SEQ ID NO: 6) (332bp; 62° C.; 40; 30s); slitrk4: Frw: 5'-TGAACTGAAGGCGAAACTGC-3' (SEQ ID NO: 7); Rev: 5'-ACAAAGCACAAAGAGACGAAG (SEQ ID NO: 8) (409bp; 64° C.; 40; 30s); slitrk5: Frw: 5'-CGTGGTATCAGGAAGGCAT-3' (SEQ ID NO: 9); Rev: 5'-ACAACAGTAGCCCCATCTTA-3' (SEQ ID NO: 10) (445bp; 62° C.; 35; 30s); slitrk6: Frw: 5'-GTAGATGAG-CAAATGAGAGAC-3' (SEQ ID NO: 11); Rev 5'-GCTTAG-GTTCTGATTGATGAC-3' (SEQ ID NO: 12) (701bp; 60° C.; 40; 60s). GAPDH: Frw: 5'-TGAAGGTCGGAGTCAACG-GATTTGGT-3' (SEQ ID NO: 13); Rev: 5'-CATGTGGGC-CATGAGGTCCACCAC (SEQ ID NO: 14) (983bp; 62° C.; 30; 60s).

Quantitative PCR (qPCR) was performed using the ABI 7500 fast System (Applied Biosystems, Foster City, Calif.) in standard mode with Taqman (Applied Biosystems). The qPCR conditions were 50° C. for 2 minutes and 95° C. for 10 minutes, followed by 40 cycles of 95° C. for 15 seconds and 60° C. for 1 minute.

The following primer/probe sets were obtained through Applied Biosystems: b-actin (endogenous control, 4326315E), slitrk1 (Hs00287530_s1), slitrk2 (Hs01028461_s1), slitrk3 (Hs01888327_s1), slitrk4 (Hs00331273_s1), slitrk5 (Hs01007362_s1), slitrk6 (Hs00536106_s1). The software used to analyze the data was SDS v. 1.3.1 (Applied Biosystems). The delta Ct method was used to obtain relative quantification, i.e. threshold cycle (Ct) values of the target gene (slitrk1-6) were normalized to the corresponding Ct value of the control gene (b-actin). Relative expression was calculated as follows: relative expression=(2-delta Ct)*10000. NTC and minus RT controls were run accordingly.

Cells were prepared for flow cytometry by blocking with 2% bovine serum albumin, fraction V (Calbiochem, Cambridge, Mass.), in PBS (Cellgro Mediatech Inc., Herndon, Va.) for 15 min on ice, washed and stained with the appropriate antibodies for 30 min on ice. After a second wash step, samples were analyzed in the flow cytometer (Beckman Coulter Cytomics FC 500). The antibodies used were human CD34 FITC (BD Biosciences, San Jose, Calif.), human CD11b PE (BD Biosciences), human CD41a PE (BD Biosciences) and human CD235a FITC (BD Biosciences).

Figure 3:
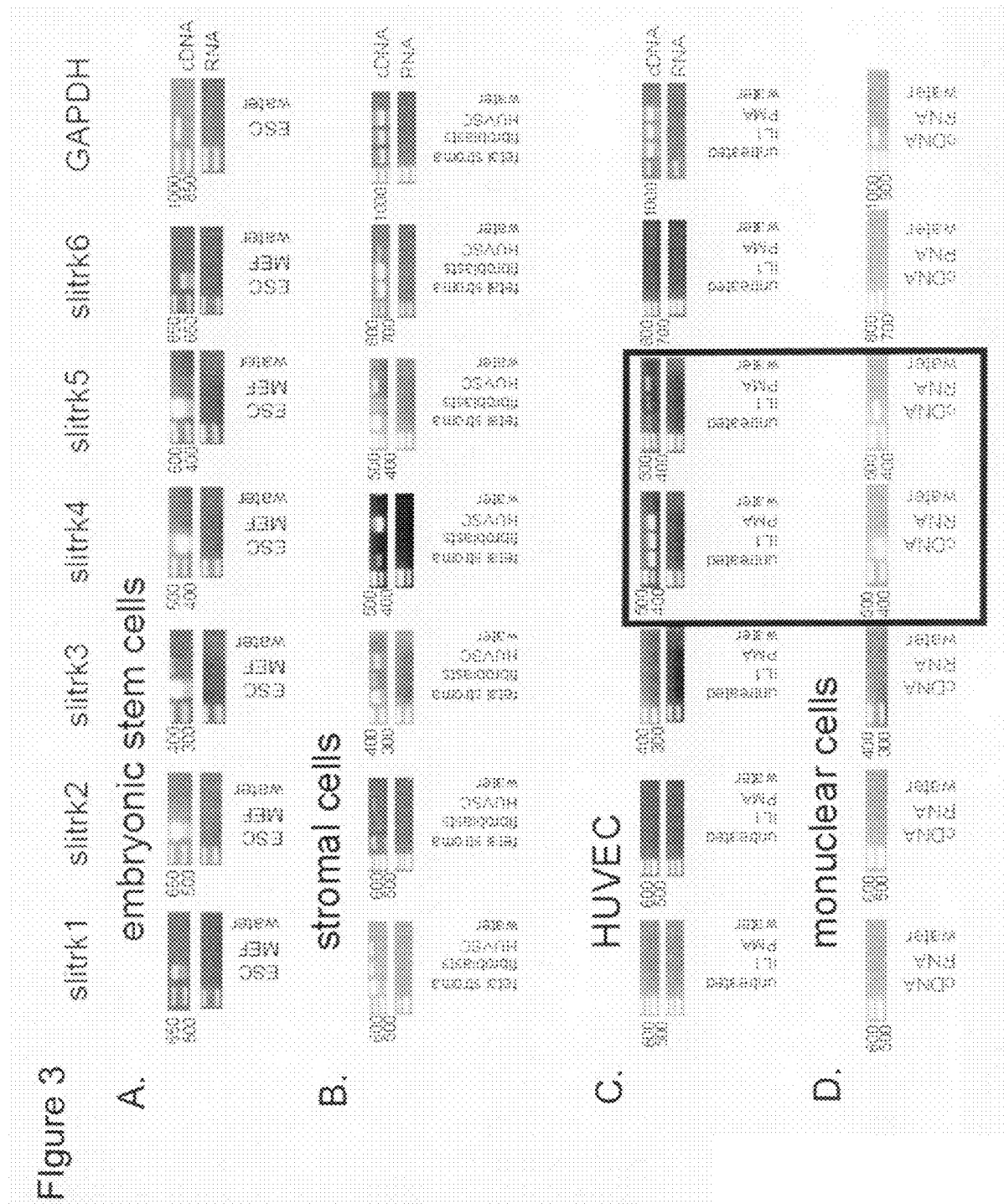
FIG. 3 shows expression of slitrk1 to slitrk6 by primary cells. RT-PCR was performed on cDNA from embryonic stem cells (ESC; panel A), fetal bone stroma, adult human foreskin fibroblasts and human umbilical vein stroma cells (HUVSC; panel B), human umbilical vein endothelial cells (HUVEC; panel C) and mononuclear cells (MNC; panel D). The frame shows the same expression pattern of slitrk4 and slitrk5 in HUVEC and MNC.

Expression of slitrk genes was assessed on human embryonic stem cells 15, human umbilical vein endothelial cells (HUVEC), mononuclear cells (MNC) isolated from peripheral blood, fetal bone stroma (BS), human foreskin fibroblast (HFF) and human umbilical vein stroma cells (HUVSC) by RT-PCR. All six members of the slitrk family were expressed by human ESC (FIG. 3A). To exclude the possibility of contamination by mouse embryonic fibroblast (MEF) feeder cells, we demonstrated that human slitrk members were not expressed by MEF using the same set of primers. Human fetal bone stroma showed a pattern similar to that of ESC, with all six members of slitrks being expressed on these cells. However, adult human foreskin fibroblasts showed a different and more specific pattern, expressing only slitrk1 and slitrk6 (FIG. 3D). This suggests that embryonic and fetal tissues maintain the expression of slitrks during development, in contrast to differentiated cells.

Analysis of slitrk expression on vascular cells revealed a highly contrasting expression pattern to that of fibroblasts. RT-PCR analysis showed that HUVEC expressed only slitrk4 and slitrk5 (FIG. 3B). Activation of HUVEC with Interleukin1 (IL1) or Phorbol-myristate-acetate (PMA) had no major effect on the expression pattern of slitrk1-slitrk6 except for a slight increase in the expression of slitrk5. Human MNC from peripheral blood of healthy donors express only slitrk4 and slitrk5, while slitrk1-slitrk3 and slitrk6 were not detected (FIG. 3D). This pattern of expression of slitrk4 and slitrk5 is identical to that detected on HUVECs.

Hematopoietic stem and progenitor cells selectively express slitrk4 and slitrk5. Hematopoietic CD34+CD38− as well as CD34+ stem and progenitor cells were sorted from human bone marrow and isolated from cord blood and mobilized peripheral blood of healthy donors respectively. Quantitative RT-PCR analysis revealed that highly purified population of human CD34+CD38− hematopoietic stem and progenitor cells isolated from bone marrow express slitrk4 and slitrk5, but not other members of the slitrk family (FIG. 4A). The CD34+CD38+ fraction also expressed slitrk4 and slitrk5, while the cells of the CD34− fraction express both genes at a very low level. Human CD34+ hematopoietic progenitor cells isolated from umbilical cord blood also expressed both slitrk4 and slitrk5, while the CD34− population expressed significantly lower levels of slitrk4 and slitrk5 (FIG. 4B). This pattern is repeated in the CD34+ and CD34− populations purified from mobilized peripheral blood of healthy donors treated with G-CSF: slitrk4 and slitrk5 were both highly expressed in the CD34+ population but only at significantly lower levels in the CD34− fraction (FIG. 4C). Similar to the expression pattern of HUVECs, slitrk1-slitrk3 and slitrk6 were not detected in any on these hematopoietic cells. This data suggests that slitrk4 and slitrk5 are highly specific for hematopoietic stem and progenitor cells.

Figure 5:
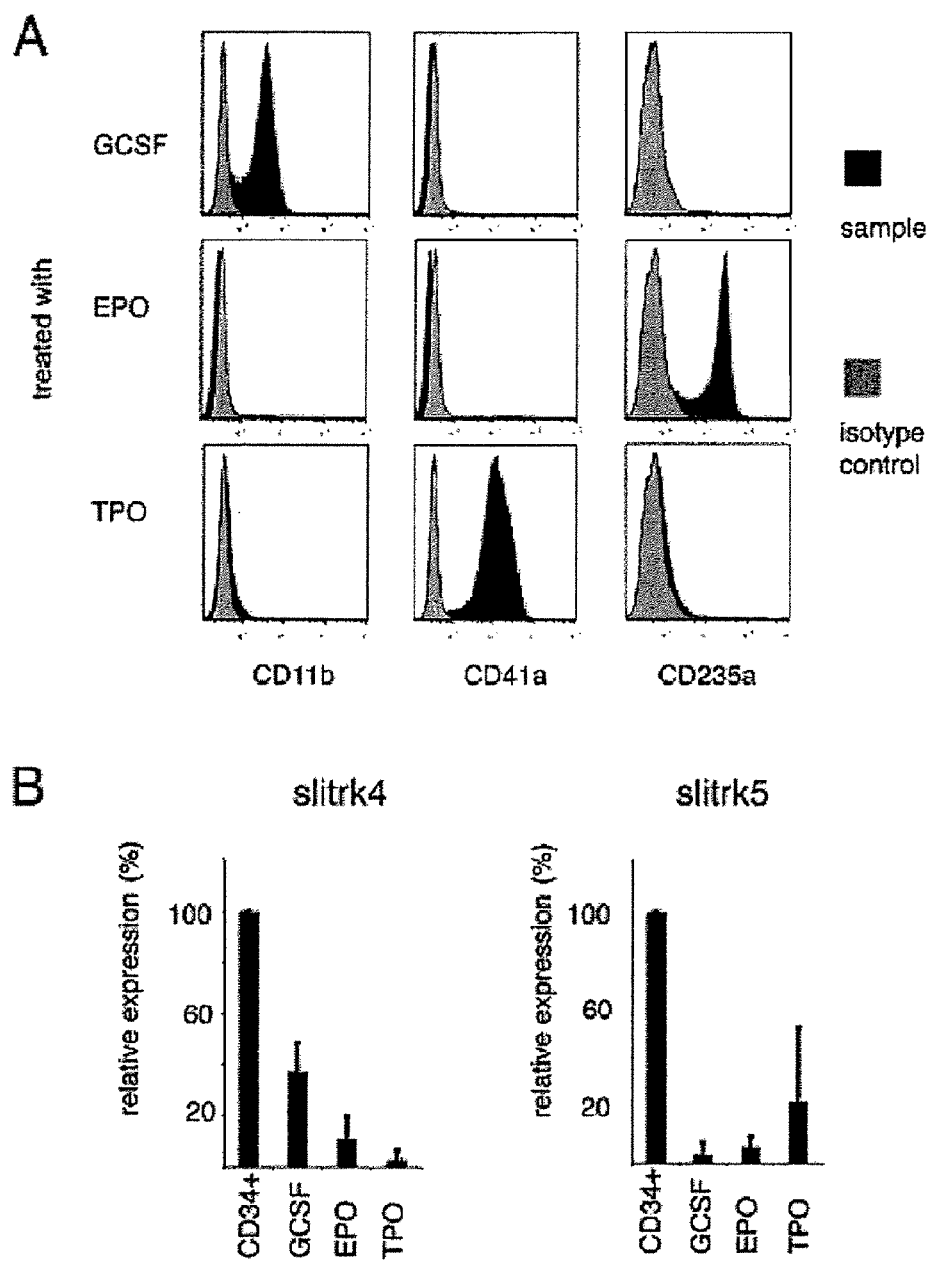
FIG. 5 shows the effect of lineage commitment of CD34+ hematopoietic progenitor cells on slitrk4 and slitrk5 expression. Panel A shows the analysis of surface markers CD11b, CD41a and CD235a by flow cytometry. Panel B shows the relative expression of slitrk4 and slitrk5 by CD34+ undifferentiated cells and in vitro differentiated cells (by qPCR). Relative expression for each group is given as a percentage of the corresponding relative expression for CD34+ cells. Error bars represent standard error of mean (n=3 independent experiments).

Expression of slitrk4 and slitrk5 is downregulated during lineage commitment. Since the CD34− fraction of expressed slitrk4 and slitrk5 only at a low level, we investigated the expression of these genes following cytokine-driven in vitro differentiation of human CD34+ cells. The CD34+ population purified from cord blood was selectively differentiated into myeloid/granulocytic, erythroid and megakaryocytic lineages using G-CSF, EPO or TPO, respectively. The phenotype of the differentiated cells was confirmed by flow cytometry using three lineage-specific markers, namely CD11b for the myeloid, CD41a for the megakaryocytic and CD235a for the erythroid lineage (FIG. 5A). Remarkably, although the undifferentiated cells showed robust expression of slitrk4 and slitrk5, the expression of these slitrks was drastically downregulated upon differentiation into the lineages analyzed. Only very low levels of slitrk4 and slitrk5 were detected on the mature CD11b+ myeloid, CD41a+ megakaryocytic or CD235a+ erythroid (FIG. 5B). These data indicate that the expression of slitrk4 and slitrk5 is restricted to immature human hematopoietic stem and progenitor cells, an expression pattern that is similar to endothelial cells.

Figure 6:
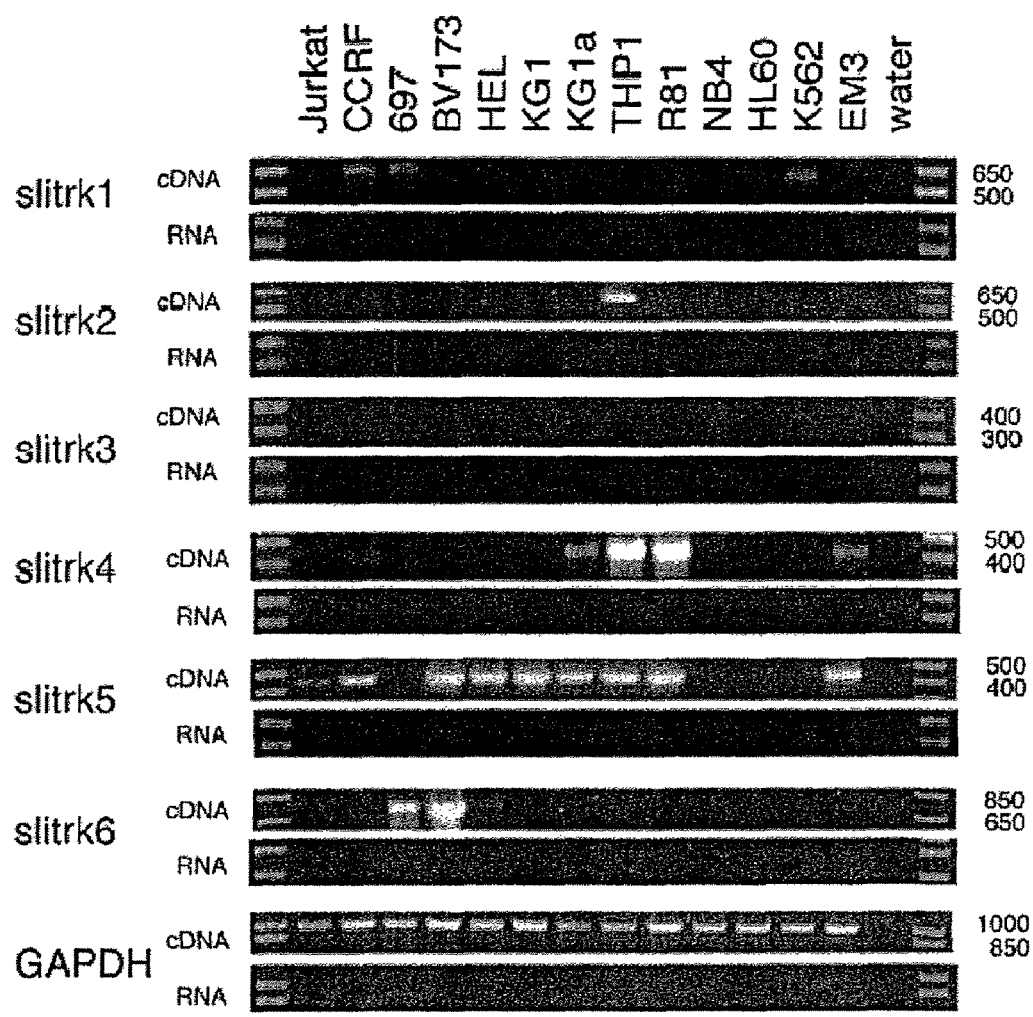
FIG. 6 shows expression of slitrk1 to slitrk6 in leukemic cell lines. Both myeloid and lymphoid subsets of the leukemic cells express various slitrks, lymphoid leukemias appear to express more slitrk1 and slitrk6, while myeloid leukemias appear to express more slitrk4 and slitrk5. None of the studied leukemic cell lines express slitrk3. The NB4 and HL60 cell lines do not express any member of the slitrks.

Differential expression of slitrk1-slitrk6 on leukemic and lymphoma cell lines. The distinct expression pattern of slitrks on hematopoietic cells led us to investigate the expression of these genes during malignant hematopoiesis. Analysis of 13 leukemic cell lines revealed that all four ALL, five out of seven AML and all of two CML cell lines express one or more members of the slitrk family (FIG. 6; Table 1). Two of the six members (slitrk4 and slitrk5) of the family are widely expressed by the leukemic cell lines (5 and 9 respectively), three members (slitrk1, slitrk2 and slitrk6) are only expressed by a few cell lines (three, one and four cell lines respectively). Only one member, slitrk3, is not detected in any of the tested leukemic cell lines. In detail, out of four lymphoblastic leukemic cell lines, two (CCRF and 697) express slitrk1, none express slitrk2 or slitrk3, one (CCRF) expresses slitrk4, three (Jurkat, CCRF and BV173) express slitrk5 and two express (697 and BV173) slitrk6. Out of the seven studied myeloid leukemic cell lines, none express slitrk1, one (THP1) expresses slitrk2, none expresses slitrk3, three (KG1a, THP1 and R81) express slitrk4, five (HEL, KG1, KG1a, THP1 and R81) express slitrk5 and one (HEL) expresses slitrk6. Comparison of the two closely related cell lines KG1 and KG1a revealed a specific expression pattern for slitrk4: it is expressed only by the undifferentiated variant KG1a, but not by the parental KG1 cell line. Regarding the chronic myeloid leukemic cell lines, one (K562) expresses slitrk1, none expresses slitrk2 or slitrk3 and one (EM3) expresses all three of slitrk4, slitrk5 and slitrk6. Only two leukemic cell lines do not express any of the slitrks, namely the myeloid leukemic cell lines NB4 and HL60 (FIG. 3; Table 1).

TABLE 1

| cell line | | slitrk1 | slitrk2 | slitrk3 | slitrk4 | slitrk5 | slitrk6 |
|---|---|---|---|---|---|---|---|
| acute lymphoblastic leukemias | | | | | | | |
| Jurkat | acute T-cell leukemia | neg | neg | neg | neg | positive | neg |
| CCRF | acute lymphoblastic leukemia | positive | neg | neg | positive | positive | neg |
| 697 | acute B-cell precursor leukemia | positive | neg | neg | neg | neg | positive |
| BV 173 | chronic B-cell precursor leukemia in blast crisis | neg | neg | neg | neg | positive | positive |
| acute myeloid leukemias | | | | | | | |
| HEL | acute erythroleukemia | neg | neg | neg | neg | positive | positive |
| KG1 | acute myeloid leukemia | neg | neg | neg | neg | positive | neg |
| KG1a | acute myeloid leukemia | neg | neg | neg | positive | positive | neg |
| THP1 | acute monocytic leukemia | neg | positive | neg | positive | positive | neg |

TABLE 1-continued

| cell line | | slitrk1 | slitrk2 | slitrk3 | slitrk4 | slitrk5 | slitrk6 |
|---|---|---|---|---|---|---|---|
| R81 | acute myeloid Leukemia | neg | neg | neg | positive | positive | neg |
| NB4 | acute promyelocytic leukemia | neg | neg | neg | neg | neg | neg |
| HL60 | acute promyelocytic leukemia | neg | neg | neg | neg | neg | neg |
| chronic myeloid leukemias | | | | | | | |
| K562 | chronic myeloid leukemia | positive | neg | neg | neg | neg | neg |
| EM3 | chronic myeloid leukemia | neg | neg | neg | positive | positive | positive |
| Burkitt B-lymphomas | | | | | | | |
| Daudi | Burkitt lymphoma | neg | neg | neg | neg | neg | neg |
| Raji | Burkitt lymphoma | positive | neg | neg | positive | neg | positive |
| GA-10 | Burkitt lymphoma | neg | neg | neg | neg | neg | neg |
| JD38 | Burkitt lymphoma | neg | neg | positive | positive | positive | positive |
| primary effusion B-lymphomas | | | | | | | |
| BC-1 | Primary effusion B cell lymphoma | positive | (positive) | neg | positive | positive | positive |
| BC-3 | Primary effusion B cell lymphoma | positive | neg | positive | positive | positive | positive |
| BCBL-1 | Primary effusion B cell lymphoma | positive | neg | positive | positive | positive | positive |
| immunoblastic B-lymphoma | | | | | | | |
| OCI-LY8 | immunoblastic B cell lymphoma | neg | (positive) | neg | neg | neg | neg |

Figure 7:
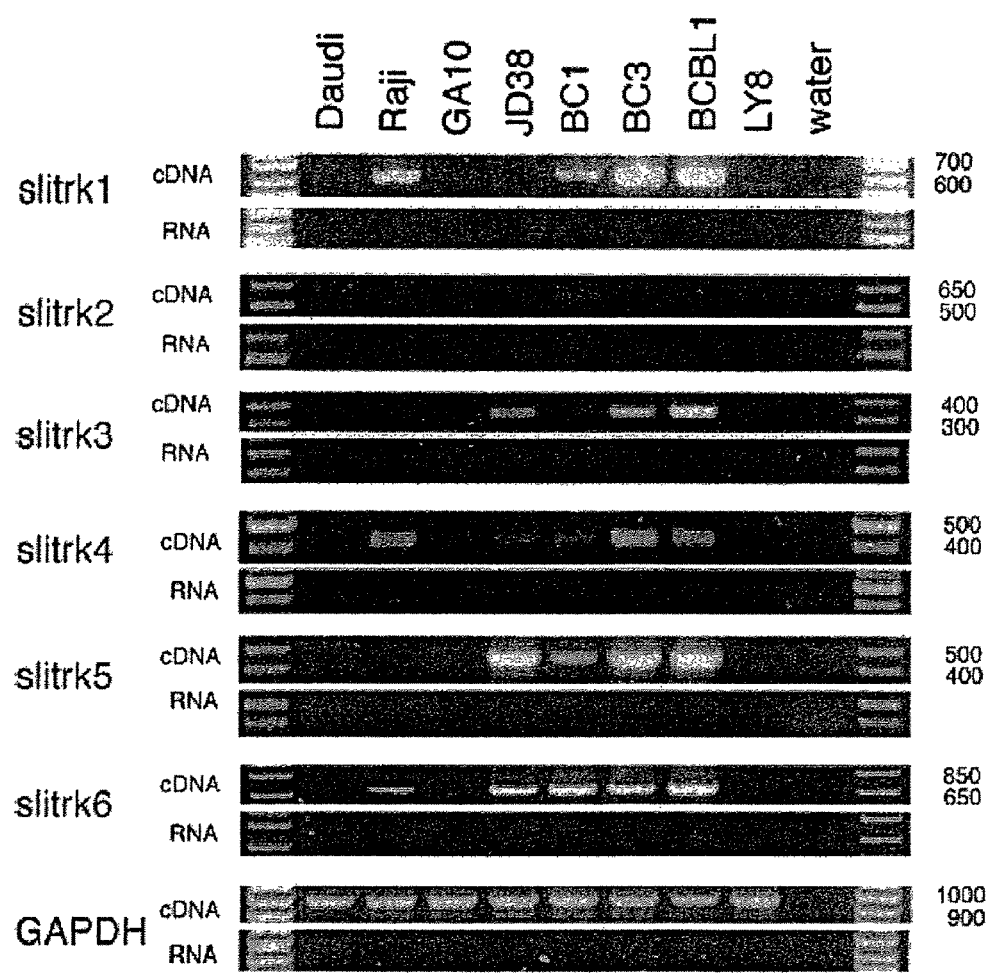
FIG. 7 shows the expression of slitrk1 to slitrk6 in lymphoma cell lines. Lymphoma cell lines express a broader range of slitrks compared to leukemic cell lines, especially PEL, which express five out of six slitrks; Daudi and GA-10 do not express any slitrk member.

The lymphoma cell lines showed a distinct expression pattern in that two (Daudi and GA10) show no expression of any of the slitrks while three cell lines (BC1, BC3 and BCBL1) show expression of five out of six slitrks (FIG. 7; Table 1). Four cell lines (Raji, BC1, BC3 and BCBL1) expressed slitrk1, two (BC-1 and OCI-Ly8) expressed slitrk2 very weakly, three (JD38, BC3 and BCBL1) expressed slitrk3, five expressed slitrk4 (Raji, JD38, BC1, BC3 and BCBL1), four expressed slitrk5 (JD38, BC1, BC3 and BCBL1) and five expressed slitrk6 (Raji, JD38, BC1, BC3 and BCBL1). Most notably, the cell lines expressing five of six slitrk members are all primary effusion lymphomas (PEL), a distinct clinical entity of diffuse body cavity-located lymphomas with no single tumor mass (18).

Although there is a clear expression pattern restricted to slitrk4 and slitrk5 in normal hematopoiesis, this is not the case in malignant hematopoiesis, as leukemic and lymphoma cell lines express a wide range of slitrks.

Identification of novel markers that could selectively discriminate hemangiogenic stem and progenitors from mesenchymal cells will provide a novel means to identify and purify these populations as well as to study the differentiation pattern of various organ-specific stem and progenitor cells during development. Here, we show for the first time that human ESC, HUVEC, MNC and stromal cells differentially express a novel class of slitrk genes, which encode for leucine-rich transmembrane proteins. Undifferentiated multi-potent cells, including human ESC and fetal bone stroma expressed all six members of the slitrk family, indicating the potential importance of slitrks for the identification of these primitive cells during developmental processes. However, the adult stem cells, including human bone marrow CD34+CD38– cells and cord blood-derived as well as mobilized CD34+ hematopoietic stem and progenitor cells, primarily expressed slitrk4 and slitrk5. In accordance, mature CD34– hematopoietic cells or lineage committed cells had significantly lower levels of the expression of slitrk4 and slitrk5. Therefore, slitrk4 and slitrk5 are predominantly expressed on undifferentiated hematopoietic cells and may constitute new markers for immature hematopoietic cells. Interestingly, we found that, similar to immature hematopoietic cells, endothelial cells only expressed slitrk4 and slitrk5, while stromal cells expressed slitrk1 and slitrk6.

Most notably, the expression pattern of slitrk4 and slitrk5 changes during differentiation of hematopoietic CD34+ cells, with both markers being significantly downregulated in terminally differentiated myeloid, megakaryocytic and erythroid cells. This suggests a role for slitrk4 and slitrk5 in the differentiation of hematopoietic cells, and as such they could be used phenotypically to identify the more pluripotent hematopoietic stem and progenitor cells.

However, we found that both slitrk4 and slitrk5 were also expressed by the human peripheral blood mononuclear cells. This signal might be generated by immature circulating cells (possibly circulating CD34+ hematopoietic or endothelial cells), or by a different as yet to be defined cellular compartment.

We also demonstrated that leukemic and lymphoma cell lines express slitrk1-slitrk6. This expression pattern contrasts that of normal hematopoietic stem and progenitor as well as mononuclear cells, which express only slitrk4 and slitrk5. This difference in slitrk expression between leukemic and lymphoma cell lines and normal hematopoiesis is possibly due to reactivation of slitrks during malignant transformation. Although no clear-cut expression pattern could be deduced, there seemed to be a trend towards lymphoblastic leukemic cells expressing more slitrk1 and slitrk6, while myeloid leukemic cells expressed more slitrk4 and slitrk5. On the other hand, in lymphomas slitrks seemed more widely expressed than in leukemias, with half of the lymphoma cell lines expressing at least four members of the slitrk family. In contrast to leukemias, which showed no expression of slitrk3, four lymphoma cell lines expressed slitrk3, while slitrk2 was only expressed weakly by two cell lines. The three PEL cell lines (BC1, BC3 and BCBL1) especially showed a higher expression of the slitrks (five out of six members expressed on each cell line) compared to the other studied lymphomas, where three out of five did not express any member of the slitrk family. This broad and differential expression of the slitrks by PEL cell lines may mirror their distinct clinical entity as well as the poorer prognosis in comparison to other lymphomas (15, 18).

Our results suggest that slitrks may be involved in embryonic development and normal as well as malignant hematopoiesis. Thus, slitrks may constitute a novel marker of embryonic stem cells and hemangiogenic stem and progenitor cells.

References for Example 2

(1) Asahara T, Murohara T, Sullivan A, et al. Isolation of putative progenitor endothelial cells for angiogenesis. Science. Feb. 14 1997; 275(5302):964-967.
(2) Osawa M, Hanada K, Hamada H, Nakauchi H. Long-term lymphohematopoietic reconstitution by a single CD34-low/negative hematopoietic stem cell. Science. Jul. 12 1996; 273(5272):242-245.
(3) Rafli S, Lyden D. Therapeutic stem and progenitor cell transplantation for organ vascularization and regeneration. Nat Med. June 2003; 9(6):702-712.
(4) Bonnet D, Dick J E. Human acute myeloid leukemia is organized as a hierarchy that originates from a primitive hematopoietic cell. Nat Med. July 1997; 3(7):730-737.
(5) Folkman J. Angiogenesis-dependent diseases. Semin Oncol. December 2001; 28(6):536-542.
(6) Civin C I, Strauss L C, Brovall C, Fackler M J, Schwartz J F, Shaper J H. Antigenic analysis of hematopoiesis. III. A hematopoietic progenitor cell surface antigen defined by a monoclonal antibody raised against KG-1a cells. J. Immunol. July 1984; 133(1):157-165.
(7) Yin A H, Miraglia S, Zanjani E D, et al. AC133, a novel marker for human hematopoietic stem and progenitor cells. Blood. Dec. 15 1997; 90(12):5002-5012.
(8) Okada S, Nakauchi H, Nagayoshi K, et al. Enrichment and characterization of murine hematopoietic stem cells that express c-kit molecule. Blood. Oct. 1 1991; 78(7):1706-1712.
(9) Baum C M, Weissman I L, Tsukamoto A S, Buckle A M, Peault B. Isolation of a candidate human hematopoietic stem-cell population. Proc Natl Acad Sci USA. Apr. 1 1992; 89(7):2804-2808.
(10) Goodell M A, Brose K, Paradis G, Conner A S, Mulligan R C. Isolation and functional properties of murine hematopoietic stem cells that are replicating in vivo. J Exp Med. Apr. 1 1996; 183(4):1797-1806.
(11) Aruga J, Mikoshiba K. Identification and characterization of Slitrk, a novel neuronal transmembrane protein family controlling neurite outgrowth. Mol Cell Neurosci. September 2003; 24(1):117-129.
(12) Aruga J, Yokota N, Mikoshiba K. Human slitrk family genes: genomic organization and expression profiling in normal brain and brain tumor tissue. Gene. Oct. 2 2003; 315:87-94.
(13) Abelson J F, Kwan K Y, O'Roak B J, et al. Sequence variants in slitrk1 are associated with Tourette's syndrome. Science. Oct. 14 2005; 310(5746):317-320.
(14) Shmelkov S V, Visser J W, Belyavsky A V. Two-dimensional gene expression fingerprinting. Anal Biochem. Mar. 1 2001; 290(1):26-35.
(15) Simonelli C, Spina M, Cinelli R, et al. Clinical features and outcome of primary effusion lymphoma in HIV-infected patients: a single-institution study. J Clin Oncol. Nov. 1 2003; 21(21):3948-3954.
(16) Park J H, Kim S J, Oh E J, et al. Establishment and maintenance of human embryonic stem cells on STO, a permanently growing cell line. Biol Reprod. December 2003; 69(6):2007-2014.
(17) Vincent L, Jin D K, Karajannis M A, et al. Fetal stromal-dependent paracrine and intracrine vascular endothelial growth factor-a/vascular endothelial growth factor receptor-1 signaling promotes proliferation and motility of human primary myeloma cells. Cancer Res. Apr. 15 2005; 65(8):3185-3192.
(18) Nador R G, Cesarman E, Chadburn A, et al. Primary effusion lymphoma: a distinct clinicopathologic entity associated with the Kaposi's sarcoma-associated herpes virus. Blood. Jul. 15 1996; 88(2):645-656.

Table 1: Expression of slitrk1-6 in leukemic cell lines as analyzed by RT-PCR. neg: negative.

We claim:

1. A method for detecting stem or progenitor cells in a tissue, a tissue sample or a cell population, comprising:
    (a) obtaining a tissue, a tissue sample or a cell population, and
    (b) determining whether the tissue, the tissue sample or the cell population contains slitrk4 mRNA, wherein the determining step comprises contacting the tissue, the tissue sample or the cell population with a primer or probe that binds to slitrk4 mRNA, and
    (c) correlating the presence of slitrk4 mRNA with the presence of stem or progenitor cells.

2. The method of claim 1, wherein the step of determining is performed using a method selected from the group consisting of RT-PCR, in situ hybridization, northern blotting, RNase protection, and any combination of one or more thereof.

3. The method of claim 1, wherein the stem or progenitor cells are adult stem cells.

4. The method of claim 3, wherein the adult stem or progenitor cells are selected from the group consisting of mononuclear cells and hematopoietic stem or progenitor cells.

5. The method of claim 4, wherein the hematopoietic stem or progenitor cells are CD34+ hematopoietic stem or progenitor cells.

6. The method of claim 1, wherein the tissue, a tissue sample or a cell population is obtained from a mammal.

7. The method of claim 6, wherein the mammal is selected from the group consisting of primates, rodents, ovine species, bovine species, porcine species, equine species, feline species and canine species.

8. The method of claim 6, wherein the mammal is a primate.

9. The method of claim 6, wherein the mammal is a human.

10. The method of claim 1 wherein the stem or progenitor cells are hemangiogenic stem or progenitor cells.

11. The method of claim 10, wherein the hemangiogenic stem or progenitor cells are hematopoietic stem or progenitor cells.

12. The method of claim 10, wherein the hemangiogenic stem or progenitor cells are endothelial stem or progenitor cells.

* * * * *

```
                        SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcctcattct caacaacaac                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccagtagga agagtcacag                                                  20

<210> SEQ ID NO 3
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 3
gacaaccttc tgctttcact                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcagtttac attcagacca                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctggagaag acaacataca                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggcacagt caaagtctca                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgaactgaag gcgaaactgc                                                   20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acaaagcaca aagagacgaa g                                                 21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued

```
                          primer

<400> SEQUENCE: 9
cgtggtatca ggaaggcat                                                  19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acaacagtag ccccatctta                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtagatgagc aaatgagaga c                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcttaggttc tgattgatga c                                               21

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgaaggtcgg agtcaacgga tttggt                                          26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catgtgggcc atgaggtcca ccac                                            24
```